United States Patent [19]

Meador

[11] Patent Number: 5,409,117

[45] Date of Patent: Apr. 25, 1995

[54] LIQUID SPECIMEN VESSEL

[75] Inventor: James W. Meador, Houston, Tex.

[73] Assignee: KVM Technologies, Inc., Houston, Tex.

[21] Appl. No.: 227,040

[22] Filed: Apr. 13, 1994

[51] Int. Cl.[6] .............................................. A61M 1/00
[52] U.S. Cl. .................................. 206/569; 128/760;
604/317; 422/61; 422/102
[58] Field of Search ....................... 206/569, 570, 438;
128/760, 762, 766, 767; 604/317, 407; 422/61,
102, 104

[56] References Cited

U.S. PATENT DOCUMENTS

| | | | |
|---|---|---|---|
| 4,458,811 | 7/1984 | Wilkinson | 206/219 |
| 4,549,655 | 10/1985 | Forsythe, Jr. et al. | 206/569 |
| 4,589,548 | 5/1986 | Fay | 206/569 X |
| 4,761,379 | 8/1988 | Williams et al. | 435/296 |
| 4,852,560 | 8/1989 | Hermann, Jr. et al. | 128/762 |
| 4,961,432 | 10/1990 | Guirguis | 128/760 |
| 4,981,144 | 1/1991 | Carels, Jr. | 128/760 |
| 4,986,322 | 1/1991 | Chibret et al. | 141/319 |
| 5,084,041 | 1/1992 | Oxley et al. | 604/410 |
| 5,088,627 | 2/1992 | Musel | 222/145 |
| 5,133,703 | 7/1992 | Boehringer et al. | 604/317 |
| 5,137,031 | 8/1992 | Guirguis | 128/762 X |
| 5,160,329 | 11/1992 | Oxley | 604/317 |
| 5,186,900 | 2/1993 | Jensen et al. | 422/104 |
| 5,217,443 | 6/1993 | Oxley | 604/317 |

*Primary Examiner*—Jacob K. Ackun
*Attorney, Agent, or Firm*—Tim L. Burgess

[57] ABSTRACT

A liquid vessel provides a means of assuring uncontaminated, multiple specimens of a liquid. Two containers are connected side-by-side by a retainer which accepts a detachable funnel assembly that directs liquid into each container. The retainer includes both a flexible serpentine connector loosely connecting collar portions of the retainer fitted to each container and a rigid portion fixing the spacing of the containers. Each container includes an bellows-like sidewall flexure, and when the funnel is removed, each is closed by a closure that includes another bellows-like sidewall flexure, a nozzle facing away from and basally open to the floor of the container, and a stiff basal projection extending to the floor of the container. Coupling members on the floor underside of the containers enable coupling of the floors of the two containers after the rigid portion of the retainer is severed. Pushing the closure of one of the containers reduces intra-chamber pressure in that container and if the containers are coupled increases intra-chamber pressure in the coupled other container. The reduced pressure prevents discharge of specimen from the one container when a nozzle in the closure of that container is opened. Compressing the volume of the container with the opened nozzle discharges an aliquot of specimen from that container through the opened nozzle.

24 Claims, 19 Drawing Sheets

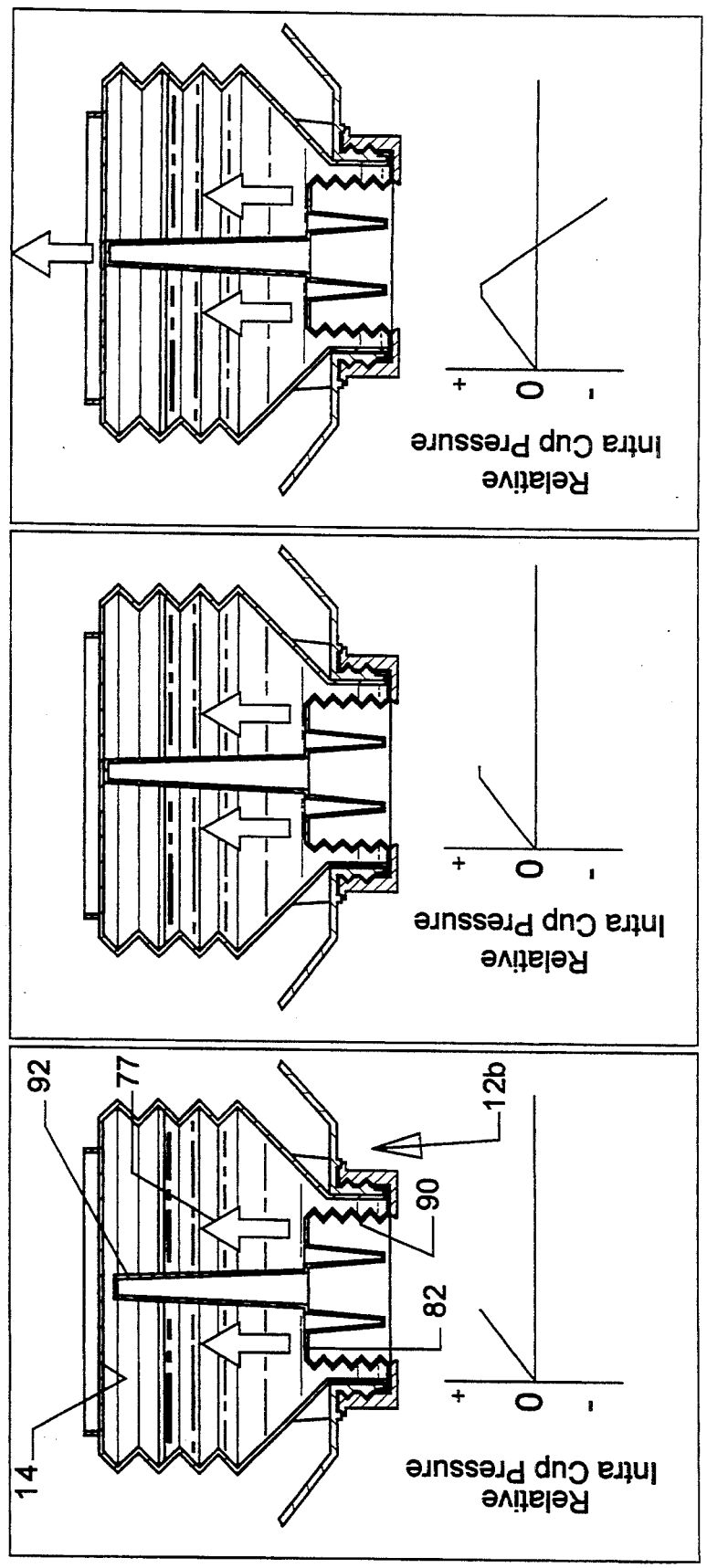

LIQUID SPECIMEN VESSEL

FIELD OF THE INVENTION

The present invention relates generally to the field of liquid sampling and testing and more particularly to a urine specimen vessel that provides for redundant isolated specimens.

BACKGROUND OF THE INVENTION

In fields such as clinical medicine, forensic sciences, environmental quality testing, food quality assurance, drug testing, and other areas, it has become possible to determine the presence and/or amount of trace substances in test samples even when such substances are present in very low concentrations (on the order of parts per million, or even per billion). For example, during testing of urine, it is now possible to detect and quantify trace quantities of most known illicit drugs. Further, as a result of such drug testing, positive test results may have a profound impact on the donor's career or employment. In the proper circumstances, positive test results may also result in criminal liability for the donor.

Such circumstances dictate that the security or chain-of-custody of the specimen be preserved and that any tampering of the specimen be immediately apparent. It is desirable that test results be verifiable by repeating the tests on an identical specimen. It is also important that the specimen be capable of being "split", in order that a secure portion of the specimen can be sent to another laboratory for independent confirmation of the test results.

Similarly, other liquid sampling procedures present the same issues of repeatability and integrity verifiability. For example, the U.S. Environmental Protection Agency conducts a variety of ongoing testing programs. These testing programs are intended to guarantee compliance with standards for maximum levels of toxic and/or radioactively contaminated liquids, such as plant effluent. In the event of a test indicating non-compliance with such a standard, it is important that the EPA be able to repeat the test on another, identical specimen. It is equally important that the EPA be able to verify that the specimen that is tested is indeed the specimen that was taken and that no foreign substances have been introduced into the specimen without being tamper evident.

Thus, there remains a need for a liquid specimen vessel that provides for more than one isolated specimen of a sample. Such a vessel should provide for splitting of the specimen for independent testing. The vessel should also minimize or even eliminate the possibility of contamination of the test specimen. Further, the vessel should automatically retain an archival specimen so that any tests may be repeated on an identical test specimen and the results of the tests verified. Such a specimen vessel should be easy to use and simple in construction. It should also present a geometric aspect that is sufficiently simple to be easily moldable by known molding techniques.

SUMMARY OF THE INVENTION

The present invention provides these and other features of a vessel for a liquid specimen, and gives a novel method of sampling a liquid specimen. The invention involves a vessel, comprising a container including a stiff floor, a sidewall connected at a lower portion of the sidewall to the floor and having an upper portion including a border surrounding an opening into the container. The sidewall further includes a flexure portion below the upper portion of the sidewall. A closure is provided for the container. The closure includes a stiff base smaller than the container opening and a closure sidewall connected at a lower portion thereof to the base. The closure sidewall has an upper portion comprising a flange extending radially outward to rest on the border of the container. The closure sidewall further includes a flexure portion below the flange portion. The closure base has a topside and a bottomside. The bottomside includes a dependent stiff projection of length to extend adjacent the container floor upon closure of the container, and the topside includes at least one upstanding nozzle opening to the bottomside.

To provide a separate isolated specimen in accordance with this invention, two of the containers and closures are interconnected by a retainer, of which at least one portion fixes the containers horizontally side-by-side and another portion loosely connects the two containers.

To facilitate filling the two interconnected containers, the invention further comprises a connectable funnel. The funnel includes a wall tapering inwardly from an upper entrance opening to two lower outlets positioned below the funnel opening, the funnel between the entrance opening and the outlets having a distributor for distributing to both the outlets a liquid admitted through the funnel entrance opening. For the connection of the funnel, the retainer interconnecting the two containers includes one member of at least one pair of companion means for releasably connecting the funnel to the retainer in position to empty liquid from the funnel outlets into the container openings in the absence of the container closures. The funnel has the other member of the at least one companion means. This other member is located exteriorly of the funnel wall for releasable connection of the funnel to the retainer.

The configuration of the vessel providing these mechanisms is advantageous in that it lends itself to being easily moldable.

The novel method of sampling will be better understood and is set forth after the description of the embodiments of the vessel and vessel assemblies which follows.

These and other objects and features of the present invention will be apparent to those of skill in the art when they read the following detailed description in conjunction with the drawing figures.

BRIEF DESCRIPTION OF THE DRAWINGS

FIGS. 19a through 19h are schematic side vertical sectional views of the one of the vessels of FIG. 18 and under each such view an x-y line graph of intra-container ("cup") historic pressure during the sequential actions on the container illustrated in FIGS. 19a through 19h.

DETAILED DESCRIPTION OF PREFERRED EMBODIMENTS

Figure 1:
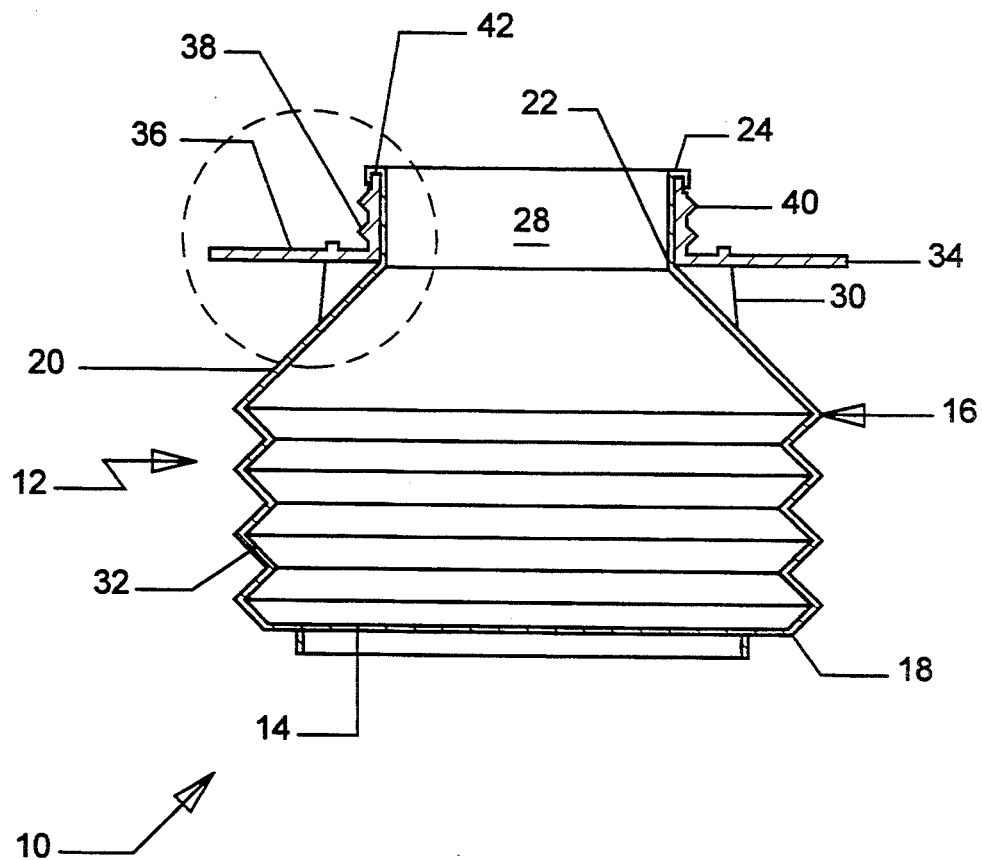
FIG. 1 is a schematic side vertical sectional view of a container and collar portion of a retainer in an embodiment of a vessel of this invention.

Referring to FIG. 1, a vessel 10 comprises a container 12 including a stiff floor 14, a sidewall 16 connected at a lower portion 18 thereof to floor 14 and having an upper portion 20 tapering inwardly to a neck 22 including a border 24 surrounding an opening or throat 28 into the interior of container 12. A retainer stop 30 is formed on the exterior circumference of taper 22. Sidewall 16 includes a flexure portion 32 below upper position 20. Sidewall flexure portion 32 suitably is a bellows or accordion-like structure in which concentric rings or pleats are molded as an expansion element. The expansion element may also take the form of a single or multi-ring spiral.

Figure 2:
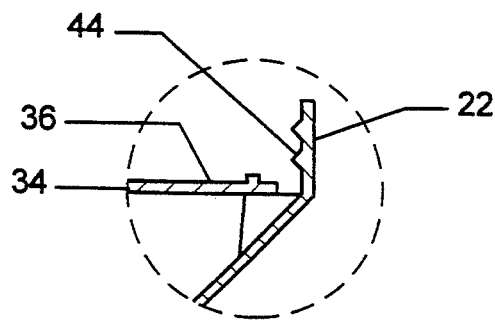
FIG. 2 is schematic side vertical sectional view of an alternative embodiment of a portion of the container and retainer portion of FIG. 1.

Surrounding container neck 22 is a retainer 34 with a collar portion 36 supported by retainer stop 30. Collar portion 36 in the embodiment depicted in FIG. 1 includes a barrel 38 surrounding the neck 24 of container 12. Collar barrel 38 has screw threads 40 formed on the exterior thereof. In this embodiment, container neck 22 is fabricated of a material that is relatively deformable and border 24 forms a gasket supported by the upper rim 42 of barrel 38. In an alternative embodiment shown in FIG. 2, container neck 22 is rigid and has screw threads 44 formed on its exterior. In this latter embodiment, retainer 34 has no barrel portion 36.

Figure 3:
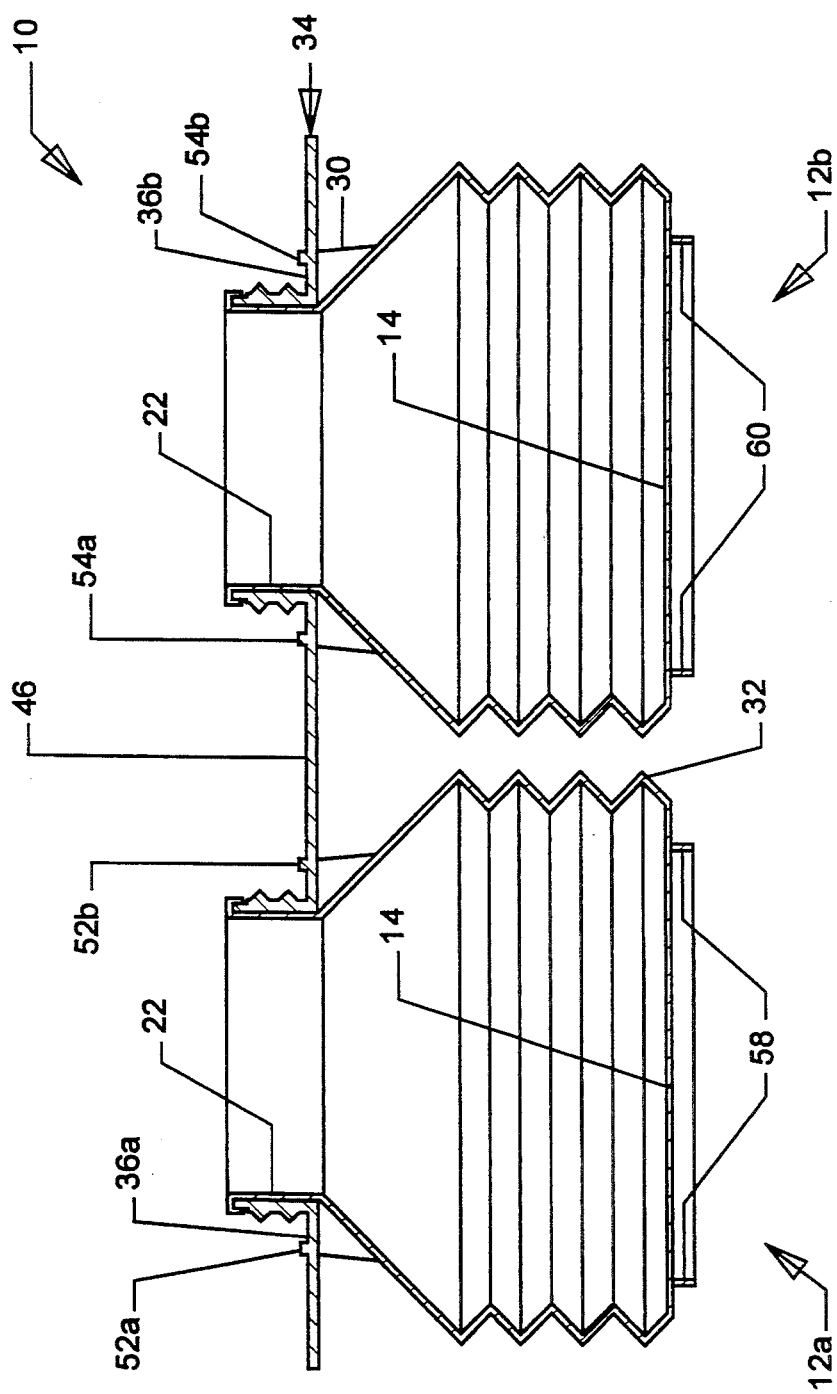
FIG. 3 is a schematic side vertical sectional view of two containers fixedly joined by a retainer of a vessel of this invention.
Figure 4:
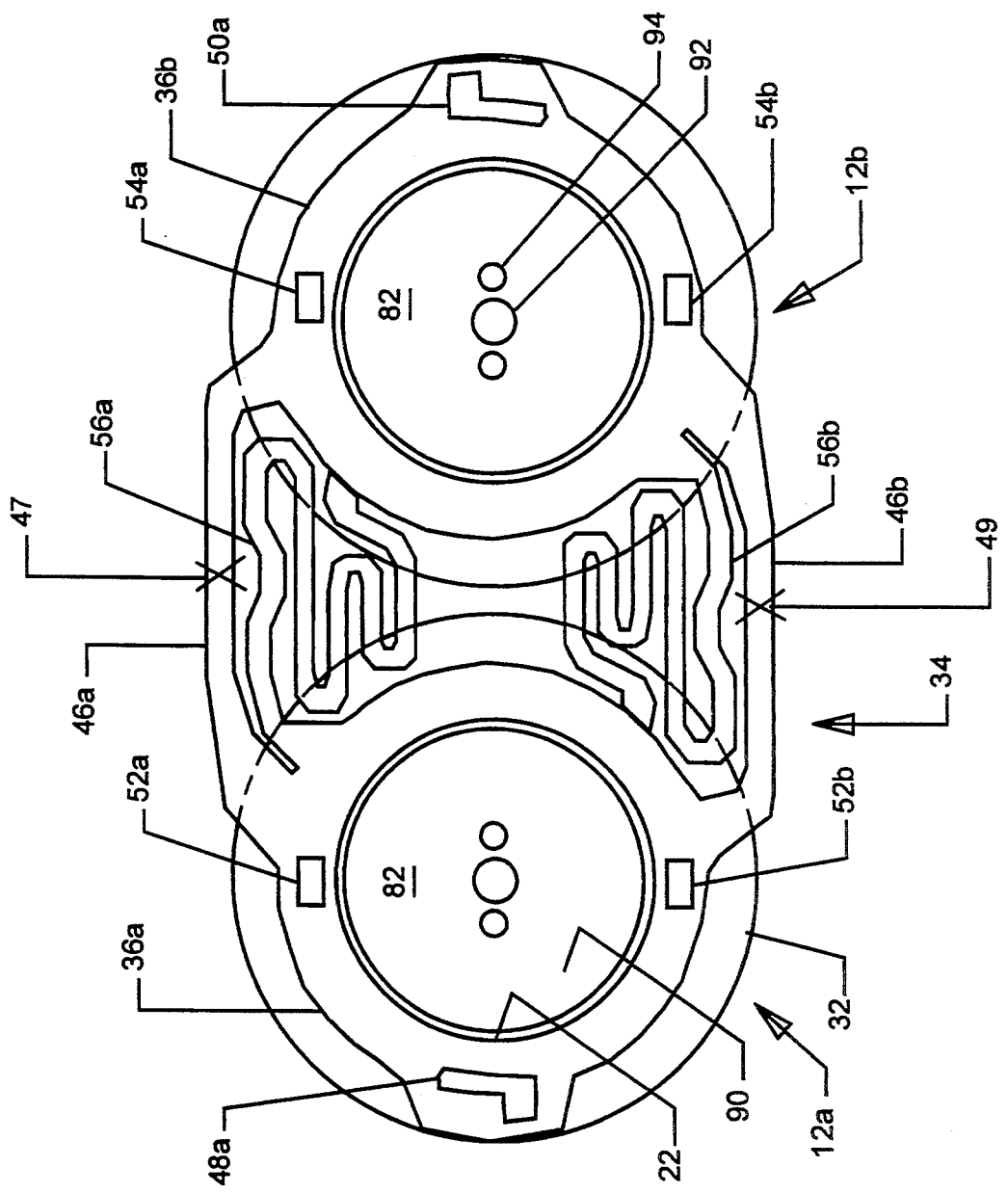
FIG. 4 is a schematic top plan view of the two joined containers of FIG. 3.

Referring to FIG. 3, retainer 34 fixingly connects two containers 12a and 12b horizontally side-by-side. Referring to FIG. 4, retainer 34 comprises collar portions 36a and 36b, rigid portions 46a and 46b fixedly connecting the two containers as shown in FIG. 3 by collar portions 36a and 36b. Retainer 34 also comprises flexible serpentine connector portions 56a and 56b loosely connecting collar portions 36a and 36b. Collar portions 36a and 36b are fitted over necks 22 of containers 12 as shown in FIGS. 1 (or 2) and 3. Collar portions 36a and 36b each include one member of at a pair of companion connectors, suitably keyway recesses 48a and 50a, and also at least one ratchet reverse turn stop 52 and 54 (52a and 52b on collar 36a, 54a and 54b on collar 36b). Stops 52 and 54 suitably are an inclined plane with the vertical wall forming the reverse turn stop, and may be situated at any radially equal location respectively on the circumference of collars 36a and 36b which does not interfere with attachment of funnel 60, described below. In FIG. 4, stops 52 and 54 are illustrated at 90 degrees rotation from their location depicted in FIGS. 1, 3, 6 and other like side sectional schematic views.

Figure 5:
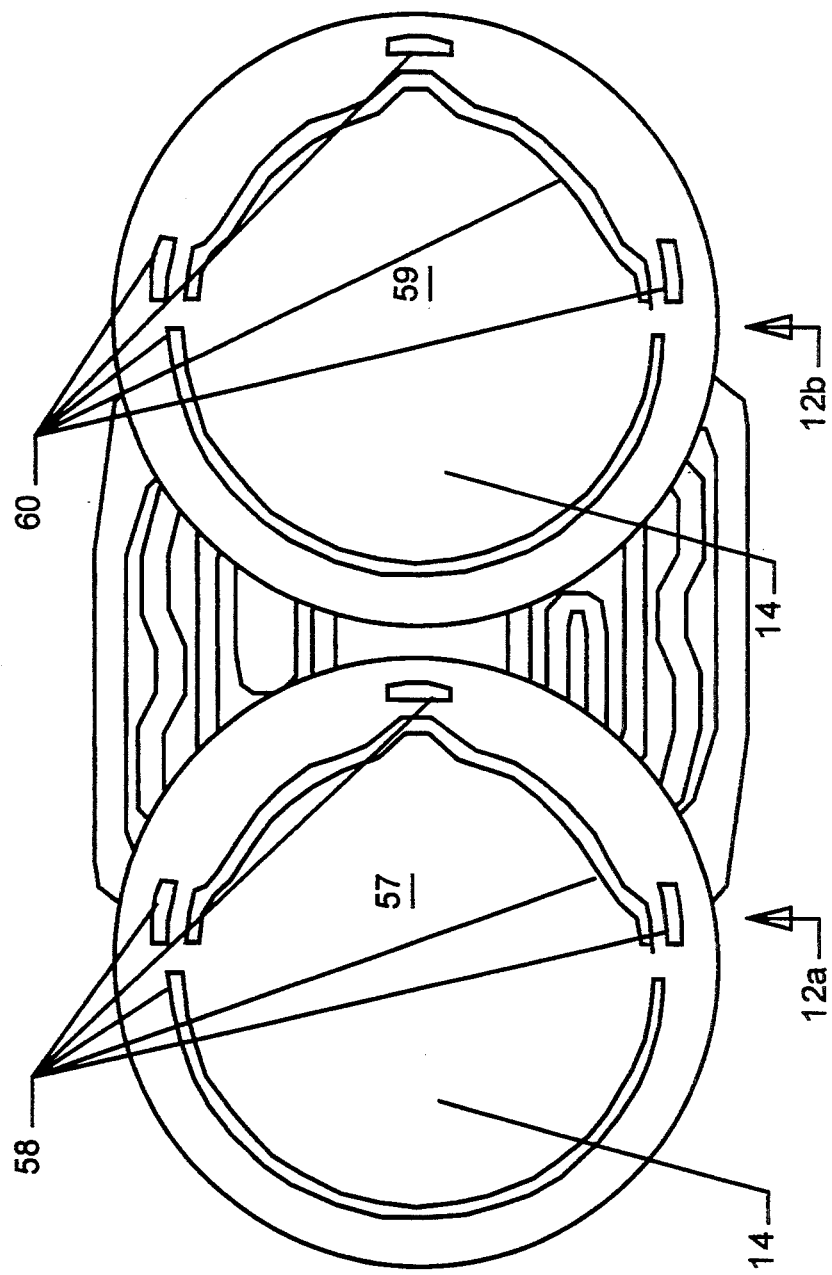
FIG. 5 is a schematic bottom plan view of two containers of a vessel assembly of this invention.

Referring to FIG. 5, a bottom view of containers 12a and 12b shows the underside of container floor 14. Floor 14 of one container (12a) has on the underside 57 thereof one member 58 of a coupling interlock and floor 14 of the other container (12b) has on the underside 59 thereof the other member 60 of the coupling interlock. Other suitable coupling devices may be used.

Figure 6:
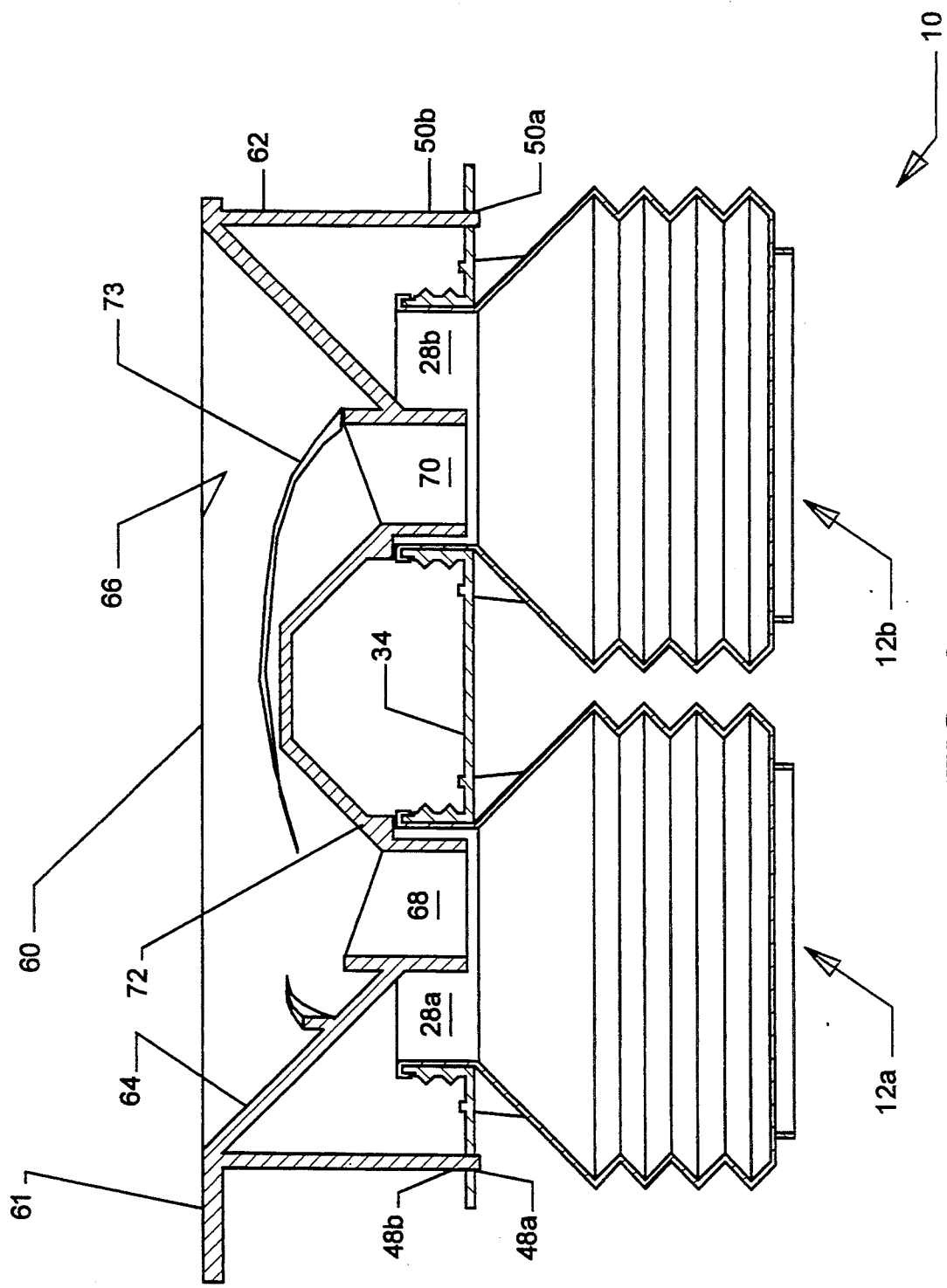
FIG. 6 is a schematic side vertical sectional view of an assembly of two containers joined by a retainer connecting a funnel of a vessel assembly of this invention.

Referring to FIG. 6, split sample vessel assembly 10 includes containers 12a and 12b fixedly connected by retainer 34 and includes a funnel 60 releasably attached to companion members 48a and 50a of retainer collar portions 36a and 36b. Funnel 60 has the other member 48b and 50b of collar companion means 48a and 50a. Funnel companion members 48b and 50b suitably are terminals depending on fingers extending from the bottom of an upper external portion of funnel wall 64. Funnel companion members 48b and 50b key into the complimentary portion of the keyway recesses 48a and 50a. With terminals 48b and 50b inserted into the complimentary portion of the keyway recesses 48a and 50a, the funnel is rotated slightly to moved terminals 48b and 50b under slot portions of the keyways which accept the fingers of companion members 48b and 50b.

Figure 7:
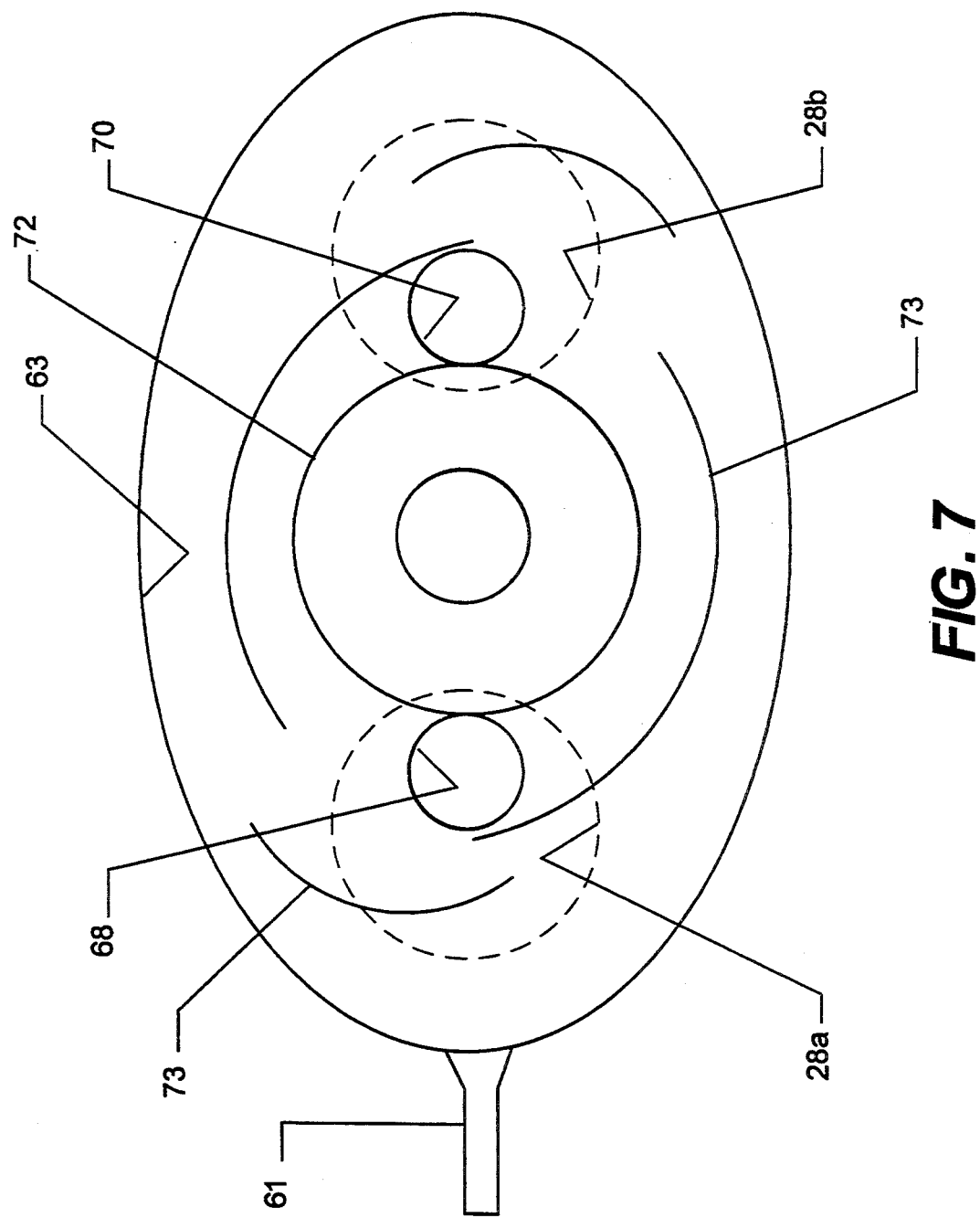
FIG. 7 is a schematic top plan view of a funnel of a vessel assembly of this invention.

Referring to FIGS. 6 and 7, funnel 60 comprises the funnel wall 64 tapering inwardly from an tipper entrance opening 66 to two lower spout outlets 68 and 70 spaced apart to empty into the spaced throats 28a and 28b of containers 12a and 12b. Between funnel entrance opening 66 and spout outlets 68, 70, a distributor 63 comprises a diverter 72 and baffles 73 for distributing flow of a liquid admitted through funnel entrance opening 66 to both spout outlets 68, 70. A series of baffles 73 which suitably overlap one of their number on one end thereof distribute entering liquid flow to both spouts 68, 70. Diverter 72 separates flow between spouts 68, 70. A handle 61 is formed at one end of the container. The handle extends in substantially the direction of a line connecting the axes of the funnel outlets. A principal intended use of the vessel assembly 10 is for urine collection and urine specimen aliquoting, and it will be appreciated that the handle makes the vessel assembly gender friendly for females. Handle 61 is illustrated schematically in a horizontal disposition, but may be angled upwardly for donor convenience.

Figure 8:
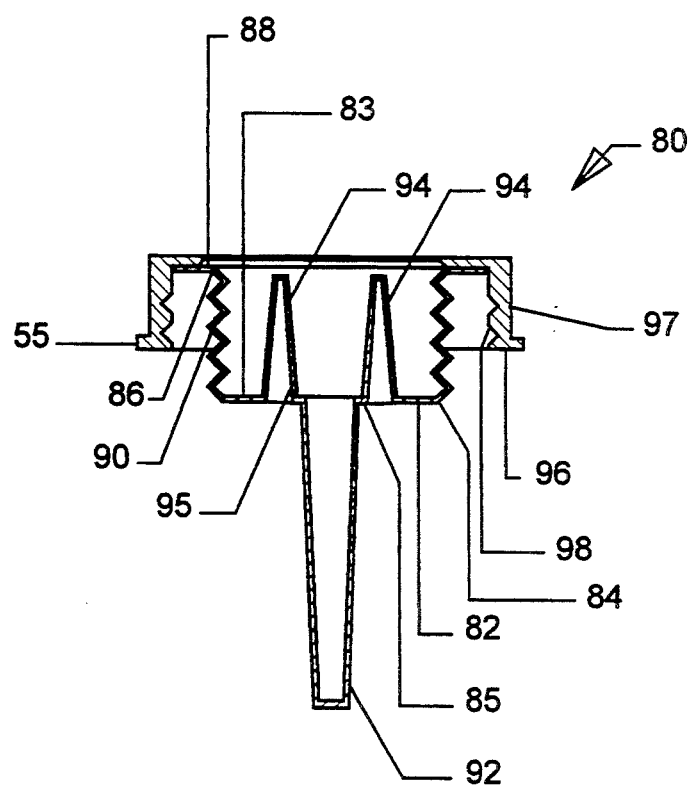
FIG. 8 is schematic side vertical sectional view of a closure cap for a container of a vessel of this invention.

Referring to FIG. 8, a closure 80 for container 12 includes a stiff base 82 smaller than the opening 28 in container 12. A sidewall 84 of closure 80 is connected at a lower portion of the sidewall to the base 82. Sidewall 84 has an upper portion 86 comprising a flange 88 extending radially outwardly to rest on the border 24 of container 12. Closure sidewall 84 further includes a flexure portion 90 below flange 88. Sidewall flexure portion 90 suitably is a bellows or accordion-like structure in which concentric rings or pleats are molded as an expansion clement. The expansion element may also take the form of a spiral.

Closure base 82 has a topside 83 and a bottomside 85. Bottomside 85 includes a dependent stiff suitably hollow projection 92 of length to extend adjacent the upperside of container floor 14 upon closure of the container. Topside 83 includes at least one upstanding nozzle 94 opening at 95 to bottomside 85.

Closure 80 also comprises a cap portion 96 with a cap rim 97 having internal threads 98 cooperative with the threads on said retainer (FIG. 1) or container neck (FIG. 1). Closure 80 includes a ratchet member 55 slideable in the forward turn direction only over ratchet reverse turn stop 52 or 54. The forward turn direction is the direction in which closure 80 is turned to screw the closure by the threads onto the container. Ratchet reverse turn stop 52 or 54 is configured to prevent a sliding movement of the cap in the reverse direction, thereby locking closure 80 onto container 12 when closure 80 is screwed on.

Container sidewall flexure portion 32 (FIG. 1) provides an intra-container pressure control regulation, assisted by closure flexure portion 90 (FIG. 8). When containers 12a and 12b are sealed with closure 80 after containers 12a and 12b are filled with liquid, the interior of the containers is at the ambient pressure of the place of filling. The containers 12a and 12b at least below the neck 22 are relatively rigid. In the absence of flexure portions 32, transfer from the place of filling to a place of higher or lower ambient pressure could cause significant pressure changes that would not be compensated by the material of the container, or by any appreciable compression by air which may be found in the primary specimen vessel. This possibly could disrupt the container sealing and cause leakage. With flexure sidewall portions 32 and 90, any pressure differential between ambient and the interior of the primary specimen vessel will equilibrate by distention or contraction of the bellows rings or pleats.

Figure 9:
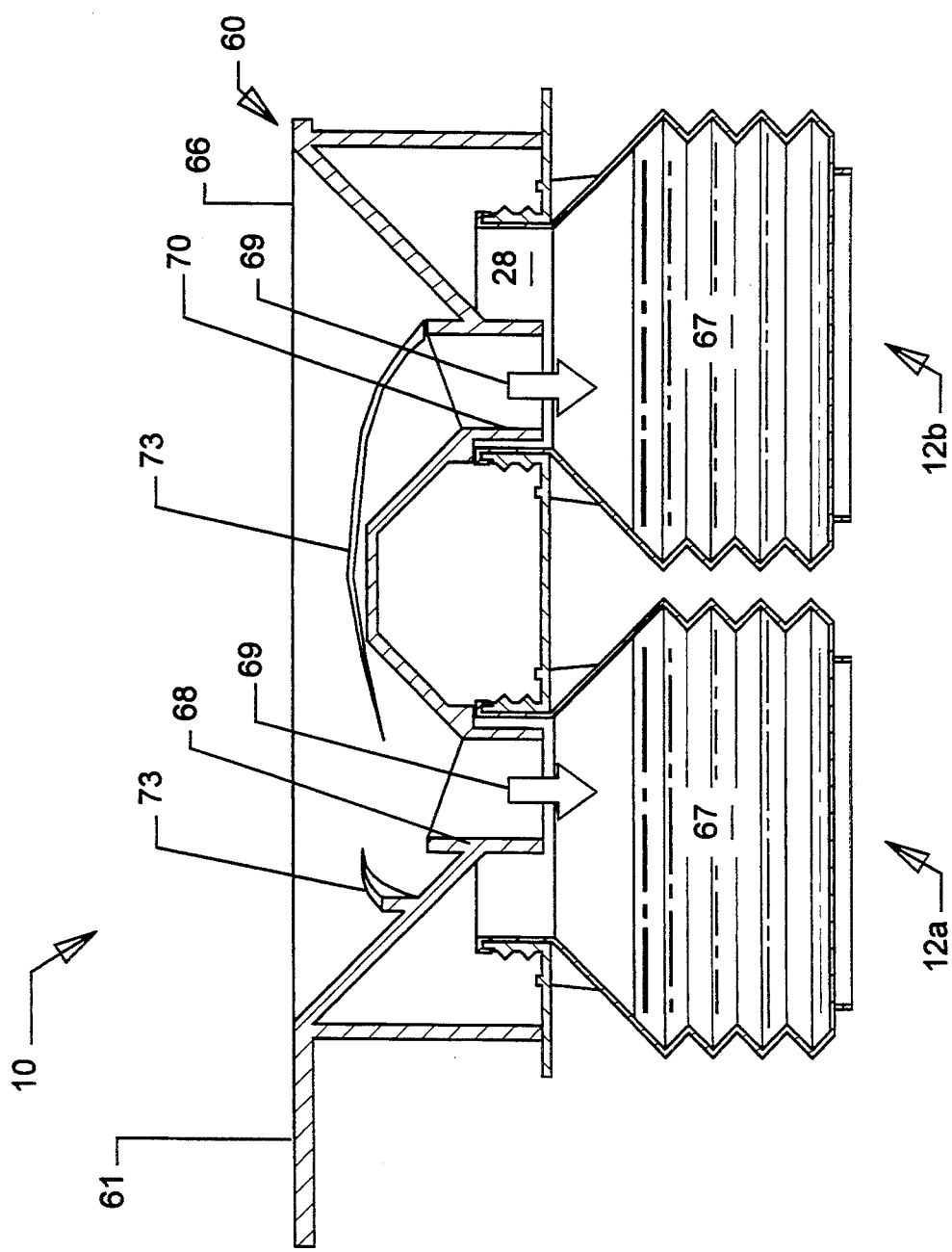
FIG. 9 is a schematic side vertical sectional view of the assembly of FIG. 6 with arrows indicating an addition of a liquid specimen to the vessel assembly.
Figure 10:
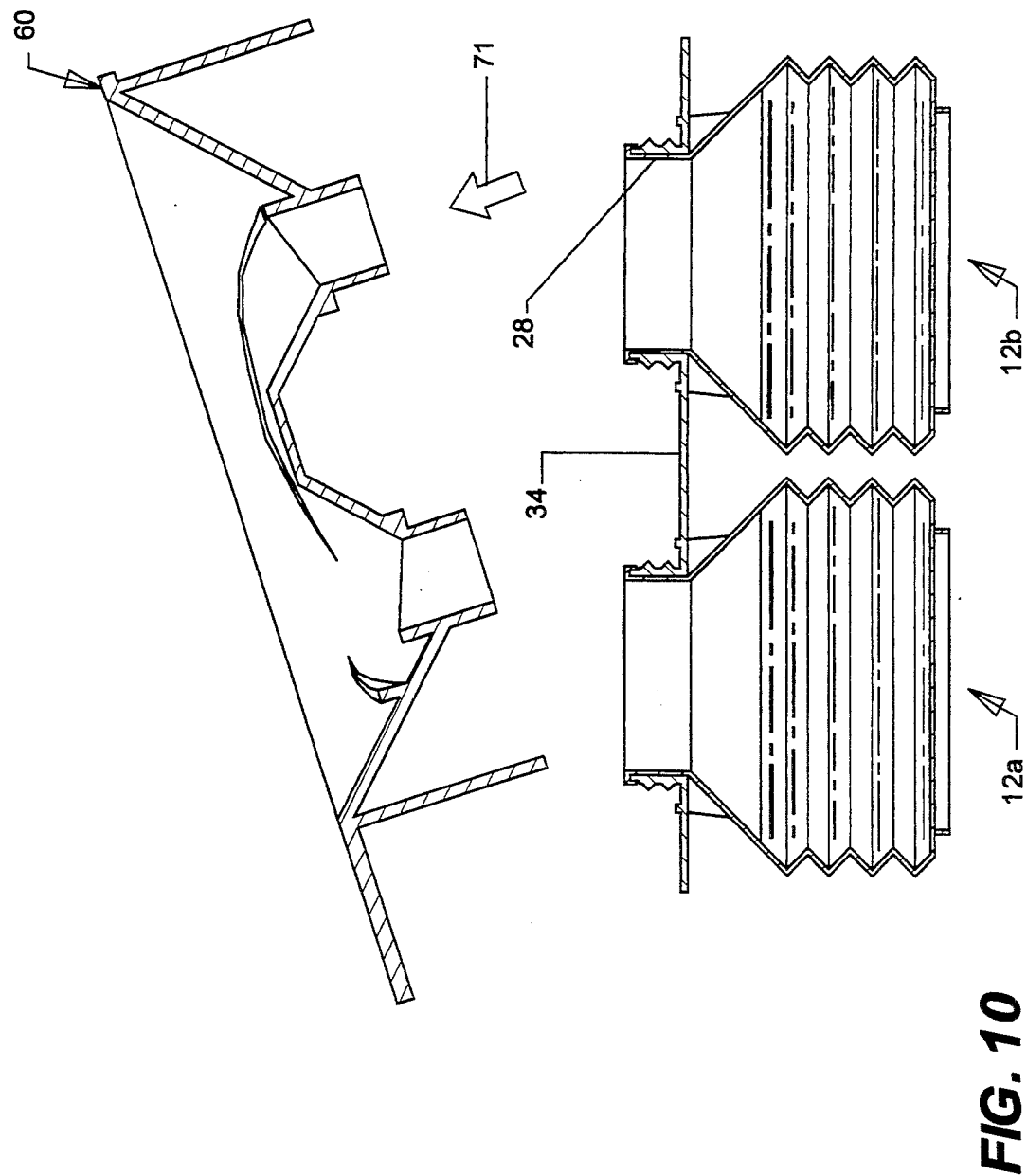
FIG. 10 is a schematic side vertical sectional view of the assembly of FIG. 9 showing a separation of the funnel portion of the vessel assembly.
Figure 11:
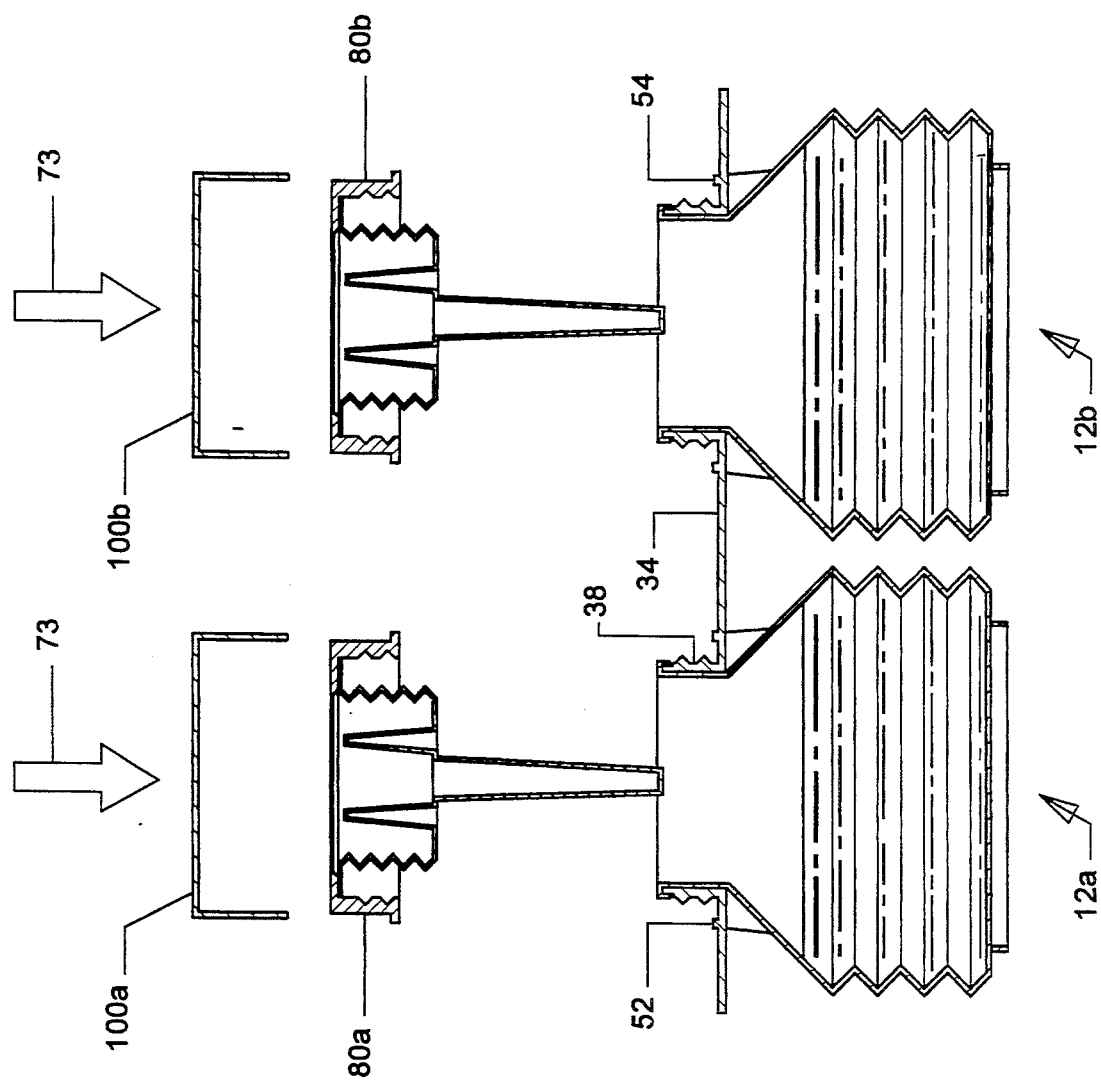
FIG. 11 is a schematic side vertical sectional view showing the caps of the vessels of this invention positioned for closure of the containers of the assembly of FIG. 10.

In the use and operation of vessel assembly 10, at a place of specimen collection a vessel assembly in the assembly state shown in FIG. 6 is removed from a sealed wrapper. In a typical chain-of-custody procedure, the donor, typically after completing a multicopy requisition, is given the vessel assembly depicted in FIG. 6. The collector retains the vessel closures 80. Referring to FIG. 9, the specimen donor privately urinates into the funnel 60 through upper entrance opening 66. Urine (indicated by numeral 67) distributed by baffles 73 and diverted by diverter 72 flows from funnel 60 through funnel as spouts 68 and 70 and container openings 28 into containers 12a and 12b, as indicated by arrows 69. The donor returns the vessel assembly inclusive of funnel 60 to the collector, who, as indicated in FIG. 10, unlocks the funnel from the vessel assembly inclusive of the containers 12a and 12b and retainer 34. This is done by rotating the funnel slightly to align the terminal extensions of funnels companion members 48b and 50b with the complimentary portion of the keyway recesses 48a and 50a and then lifting the funnel from the retainer recesses 48a and 50a, as indicated by arrow 71. The collector discards the funnel. Referring to FIG. 11, the collector then closes the containers 12a and 12b, as indicated by arrows 73, using closures 80a and 80b, by screwing the closures onto collar barrel 38 in the embodiment illustrated. The action of the cap ratchet 55 and ratchet stops 52,54 locks the cap to the container collar 36. The collector then suitably may place a tamper evident tape 100 across each closure cap 80 and onto the sides of containers 12 (tapes 100a and 100b on caps 80a and 80b of containers 12a and 12b in FIG. 11). The donor typically initials a tape 100. Split sample vessel assembly 10 comprising the containers 12a and 12b connected by retainer 34 and closed by closures 80 is now ready for delivery to a testing laboratory.

For delivery, typically a split sample vessel assembly 10 is placed in one compartment of a two compartment mailing pouch. The requisition is typically signed by the donor and collector, a copy of it is given to the donor and a file copy is retained by the collector. The remainder of the requisition typically is placed in the second compartment of the pouch. The pouch is then sealed and delivered to a testing laboratory, where a specimen or aliquot of the specimen in the vessel assembly will be removed for analytical testing. Bellows 32 permits containers 12a and 12b to expand or contract upon exposure of the vessel assembly to any materially lower or higher ambient pressure either during transit or at the destination. Bellows 32 therefore assures that the ambient pressure changes to which split sample vessel assembly 10 is exposed do not cause the vessel to leak.

Figure 12:
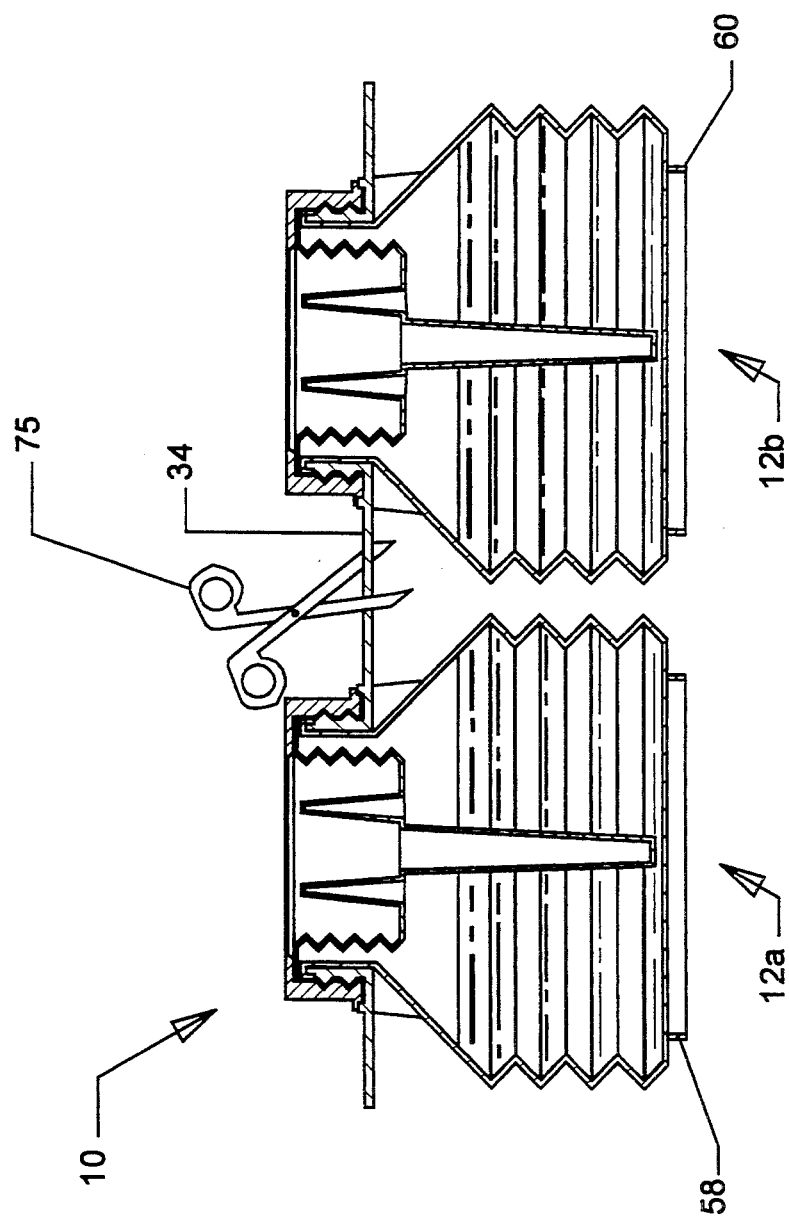
FIG. 12 is a schematic side vertical sectional view of the vessels of this invention closed with caps after removal of the funnel, with scissors indicating severance of a fixing portion of the retainer illustrated in FIG. 4.
Figure 13:
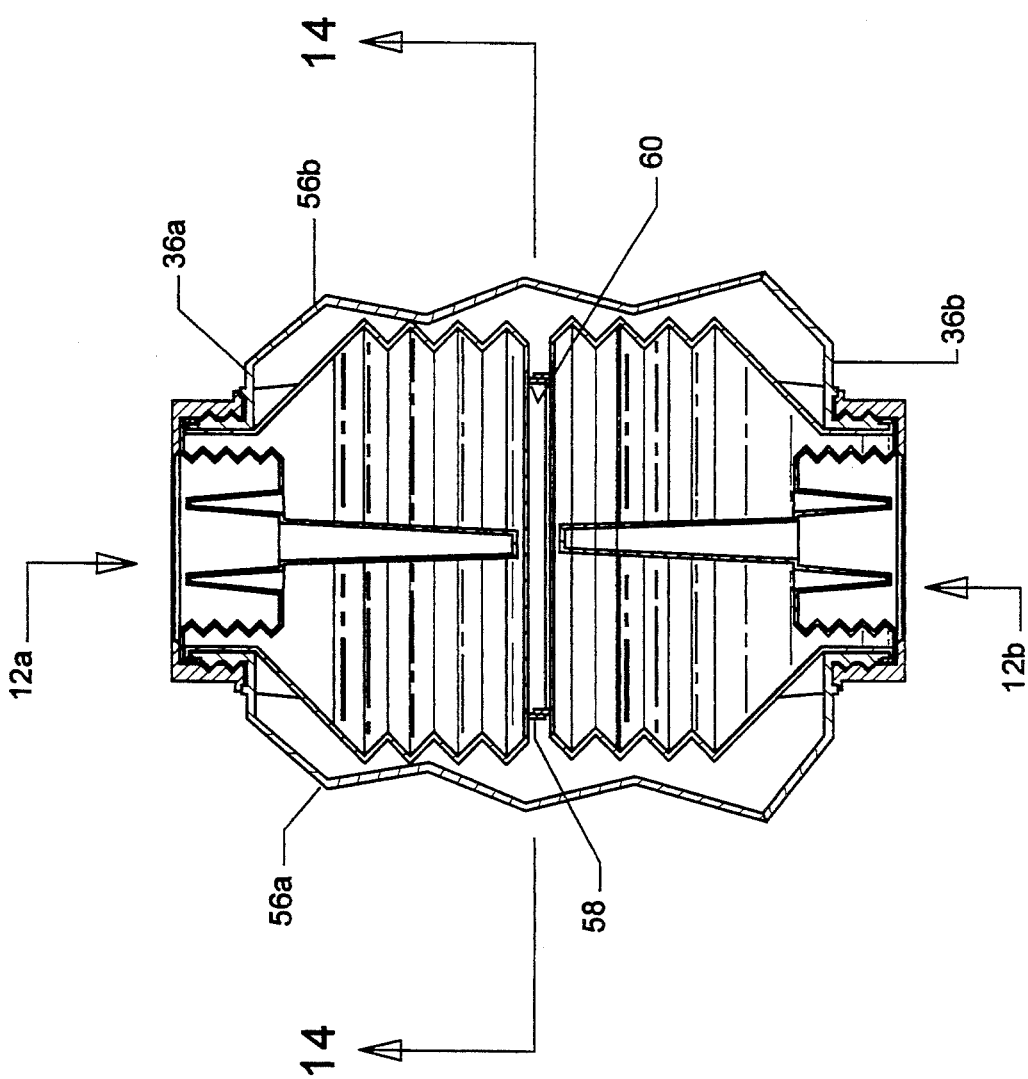
FIG. 13 is a schematic side vertical sectional view of the vessels of this invention interconnected at the floor of the containers and linked by a serpentine portion of the retainer illustrated in FIG. 4.
Figure 15:
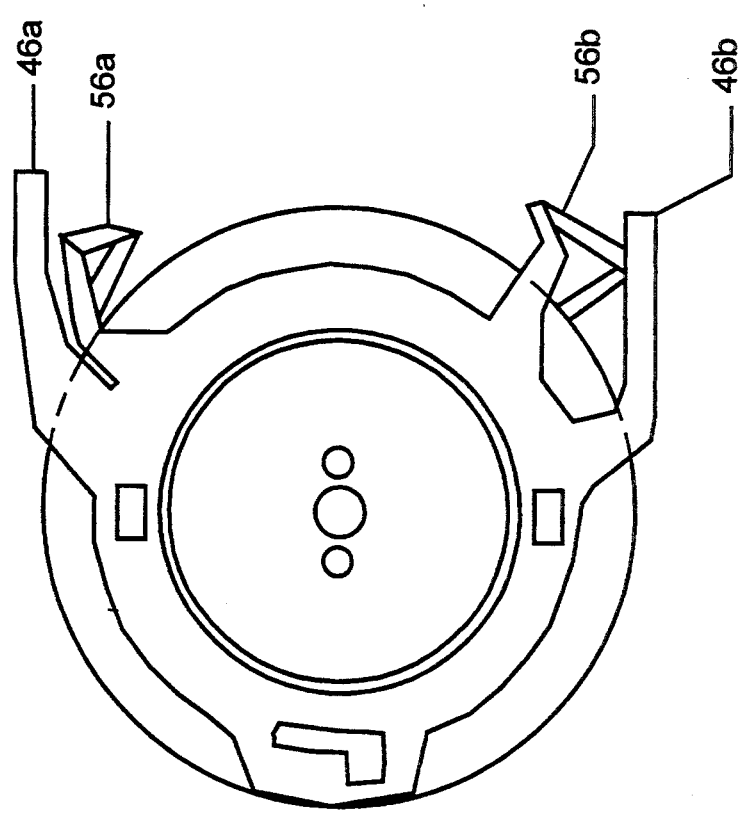
FIG. 15 is a schematic top plan view of the severed retainer of FIG. 5 attached to the top containers in FIG. 13.
Figure 14:
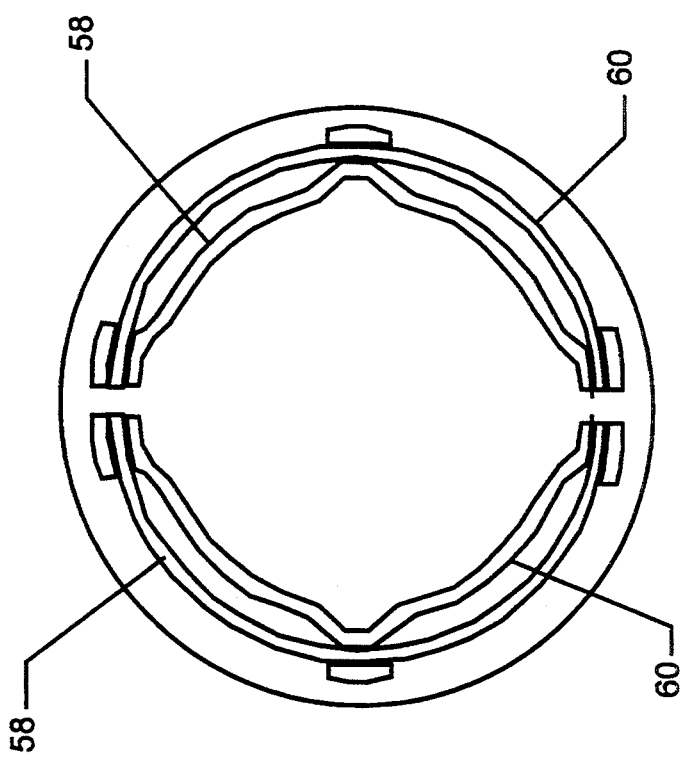
FIG. 14 is a schematic bottom plan view taken along the line 14—14 of FIG. 13 illustrating the coupling of the container interlock shown in FIG. 5.
Figure 16:
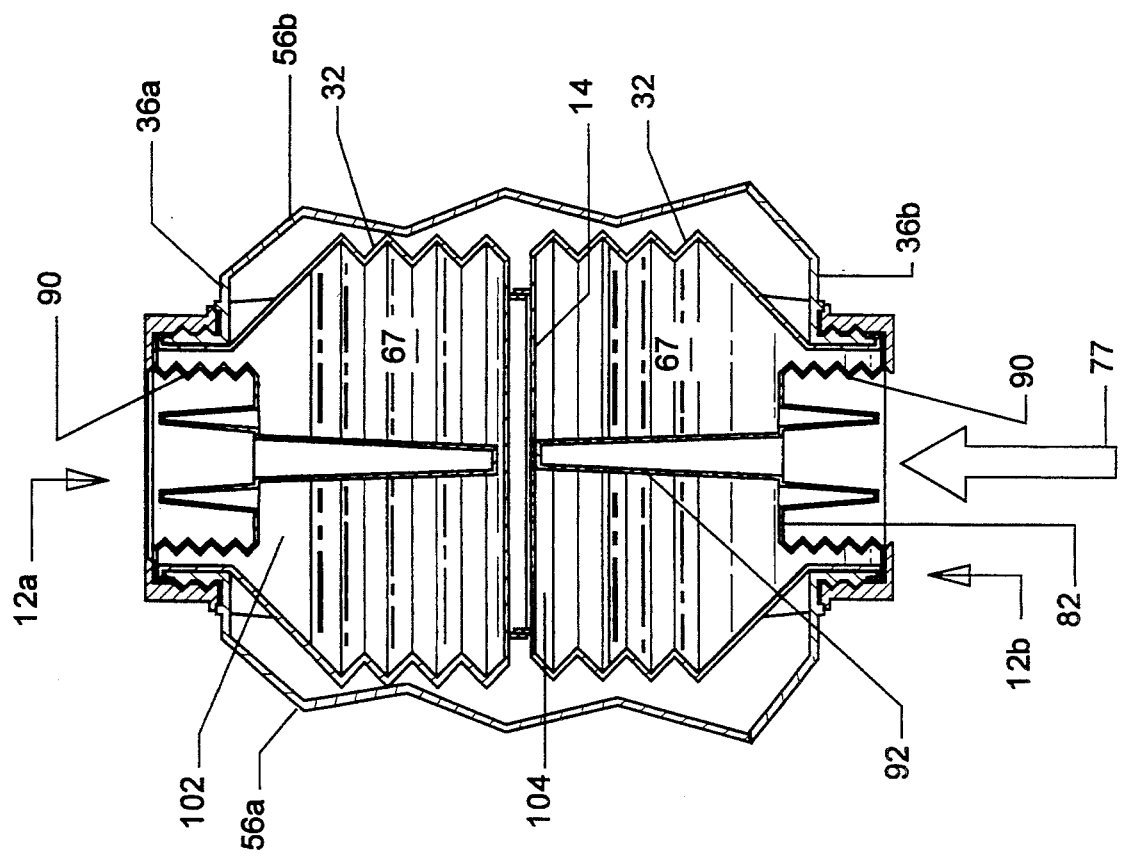
FIG. 16 is a schematic side vertical sectional view of the vessels of FIG. 13 with an arrow indicating a direction of force applied to the base of the closure of the bottom container.

At the destination, the testing laboratory continues assurance of chain-of-custody of the vessel assembly. Typically a technician removes the vessel assembly and the requisition from the pouch and attaches identical bar code labels from a set, one to the requisition, one to container 12a and another to container 12b. The same label on containers 12a and 12b assures that identification of the specimen in container 12a is the same as in container 12b. As indicated by the scissors 75 in FIG. 12, the rigid distance fixing portions 46a and 46b are severed by a technician. A severance location is indicated at 47, 49 of FIG. 4. Referring to FIGS. 13, 14 and 15, one of the containers 12a and 12b is then inverted, say 12b, and members 58 and 60 of the coupling interlock pair on the floor undersides of containers 12a and 12b are coupled, as seen in FIG. 13. Coupled, they appear as in FIG. 14. Serpentine connectors 56a and 56b interconnect the collar portions of retainer 34. The severed fixing portions 46a and 46b are seen in FIG. 15, as are the serpentine connectors 56a and 56b. While two serpentine connectors are shown, one is suitable. Referring to FIG. 16, it will be seen that any air captured in the container when it is closed is above the top surface of the urine in upright container 12a (and in the example illustrated, below base 82 of closure 80 of container 12a) as indicated by reference numeral 102. In inverted container 12b, any captured air is interposed between the top surface of the urine and floor 14 of container 12b, as indicated by reference numeral 104.

Alternative to the foregoing division of vessel assembly manipulation between the collector and the destination technician, the collector may sever the fixing portions 46a and 46b, invert one of the containers 12a and 12b and couple them, leaving them attached by serpentine connectors 56a and 56b, and then place the coupled and attached containers 12a and 12b in the delivery pouch. In such instance, upon arrival of the coupled and attached containers 12a and 12b at the place of destination, the bar code or other suitable labels are affixed to the containers 12a and 12b as already described.

After the foregoing manipulations of the split sample vessel assembly by either example, the tamper proof tape 100 is then removed from inverted container 12b, as seen in FIG. 16, exposing base 82. Vessel assembly 10 is now ready for actuation for removal of an aliquot from the split urine specimen in container 12b.

As has been described above, projection 92 from the bottomside 85 of closure base 82 extends adjacent container floor 14. The term "adjacent" is intended to include both an embodiment in which the end of projection 92 approaches near but does not contact the upperside of floor 14, as well as an embodiment in which the end of projection 92 contacts the upperside of floor 14. The former embodiment is preferred and its use and action will be described first. The pushing and pulling manipulations on container 12b described below suitably are accomplished by reciprocation of a shaft with an expandable end that inserts into hollow projection 92 and expands to grip projection 92. The shaft is not shown.

As the first action for removal of an aliquot specimen from a container 12b, negative intra-container pressure relative to the ambient pressure is increased or induced in container 12b by increasing the volume of container 12b. Referring to FIGS. 19a-19e, the sequence of how this preferably is accomplished is illustrated.

In FIG. 19a, as indicated by arrow 77, closure base 82 is pushed toward floor 14 of container 12b. This compresses any air entrapped in container 12b as at 104, reduces the volume in container 12b, and increases intra-chamber pressure, as indicated by the line graph of pressure per step below the schematic of the step, in FIG. 19a. This also lengthens the flexure or bellows portion 90 of closure 80, allowing projection 92 to move into contact with floor 14, as in FIG. 19b. After projection 92 contacts floor 14, further upward movement of projection 92, as depicted in FIG. 19c, extends both closure bellows 90 and container bellows 32. This increases the volume of container 12b, and because container 12b is sealed, a negative (or if already negative, a more negative) intra-container pressure is induced relative to the ambient pressure, as depicted by the line graph of FIG. 19c.

As illustrated in FIG. 16 for the coupled split specimen vessel assembly, movement of floor 14 of container 12b at the same time also pushes coupled floor 14 of container 12a toward base 82 of container 12a. If upward movement of container 12a is restrained, this shortens first bellows portion 90 of closure 80 and any air entrapped in container 12a at 102 is compressed. If floor 14 of container 12a is moved up into contact with projection 92 of container 12a, container bellows 32 of container 12a is contracted, and if floor 14 of container 12a is moved further upward, the volume in container 12a is reduced, increasing the intra-chamber pressure in container 12a.

Figure 19F:
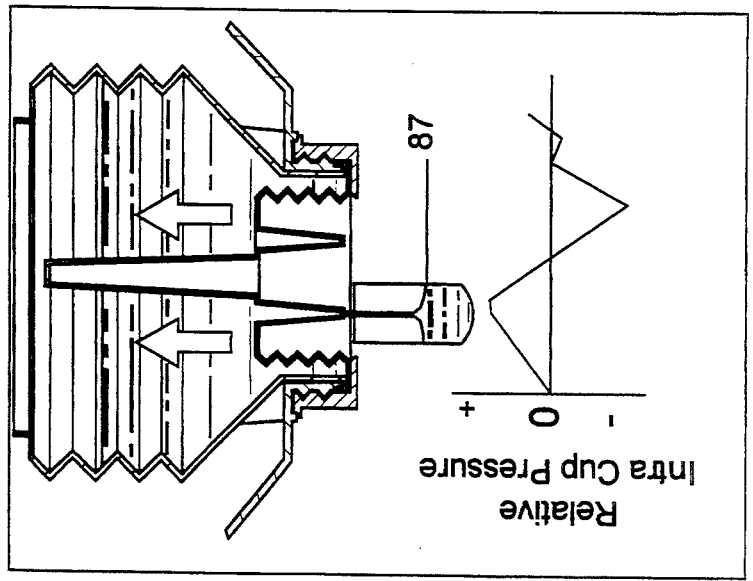

The stiffness of base 82 is sufficient to assure that when base 82 is moved upward, nozzles 94 are maintained in a substantially vertical orientation for ease of opening. With the negative pressure induced in container 12b maintained, as indicated in FIG. 19d, nozzle 94 is opened, preferably non-invasively to assure that anything which can carry a contaminant is not brought into contact with the specimen during the closure opening procedure. By non-invasively creating a hole in the nozzle closure, the integrity of the specimen in container 12b is preserved. A laser system or suitably also a pencil column of heated air may be used to open nozzle 94 non-invasively.

For example, in using a laser system, suitably a laser lens is centered in a laser beam axis to focus the focal point of the lens on the closed end of nozzle 94 placed in coaxial alignment with the laser beam axis. A laser beam shutter is then moved out of the laser beam path and the laser is powered. With the shutter open, the laser emits a beam which is focused by the laser lens onto the closed end of nozzle 94. The laser energy heats the nozzle closure and melts an opening in the closure.

The opening of the nozzle closure breaches the means of maintaining the pressure differential created by the increased volume created in container 12b. Ambient air at higher pressure rushes upwardly into the nozzle opening and duct into container 12b to equilibrate pressure, as illustrated by the line graph of FIG. 19d. This influx of gas and any bubbles formed in the duct by the entering air prevents immediate release of liquid from opened nozzle 94. Preferably the ratio of the pierced opening diameter to the length of the nozzle duct is maintained sufficiently small also to contribute to resistance of liquid flow from the opened nozzle. After a sufficient exposure time of melt an opening, a laser shutter is moved across the beam and the laser is powered down.

Figure 19E:
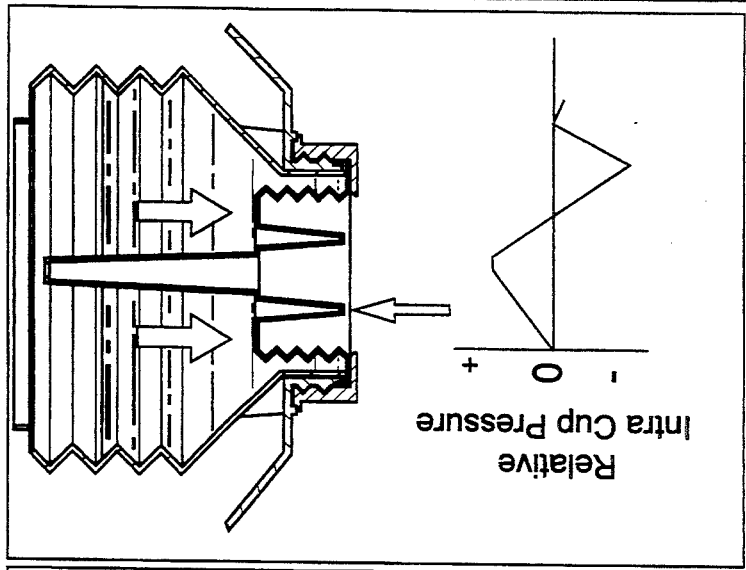
Figure 19D:
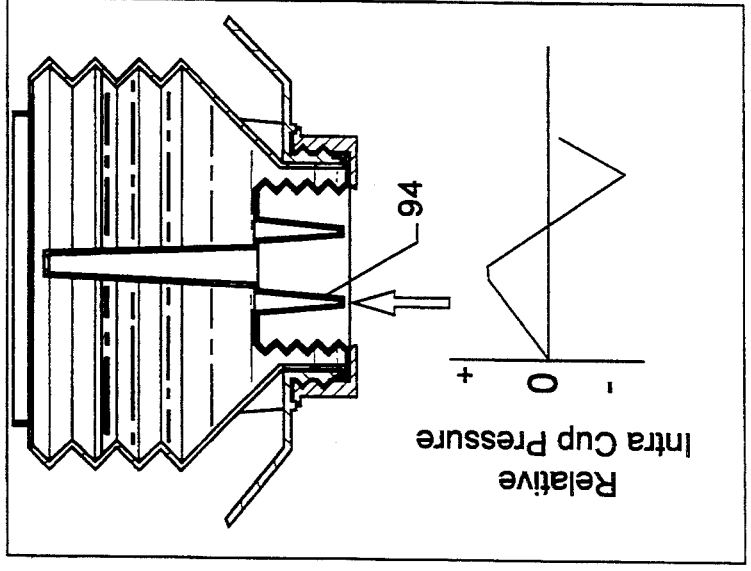

Next, as depicted in FIG. 19e, base 82 is pulled down slightly, shortening closure bellows 90 of container 12b and disengaging projection 92 of container 12b from floor 14 of container 12b. As projection 92 of container 12b withdraws, bellows 32 of container 12b shortens and resumes its native position. The opening created in the nozzle is such that the aspect of the opening to the length of the nozzle, optionally aided by air bubbles drawn into the nozzle when the nozzle is opened, provides a surface tension sufficient to retain liquid in the container during the disengagement of projection 92 from floor 14 of base 12b.

Figure 17:
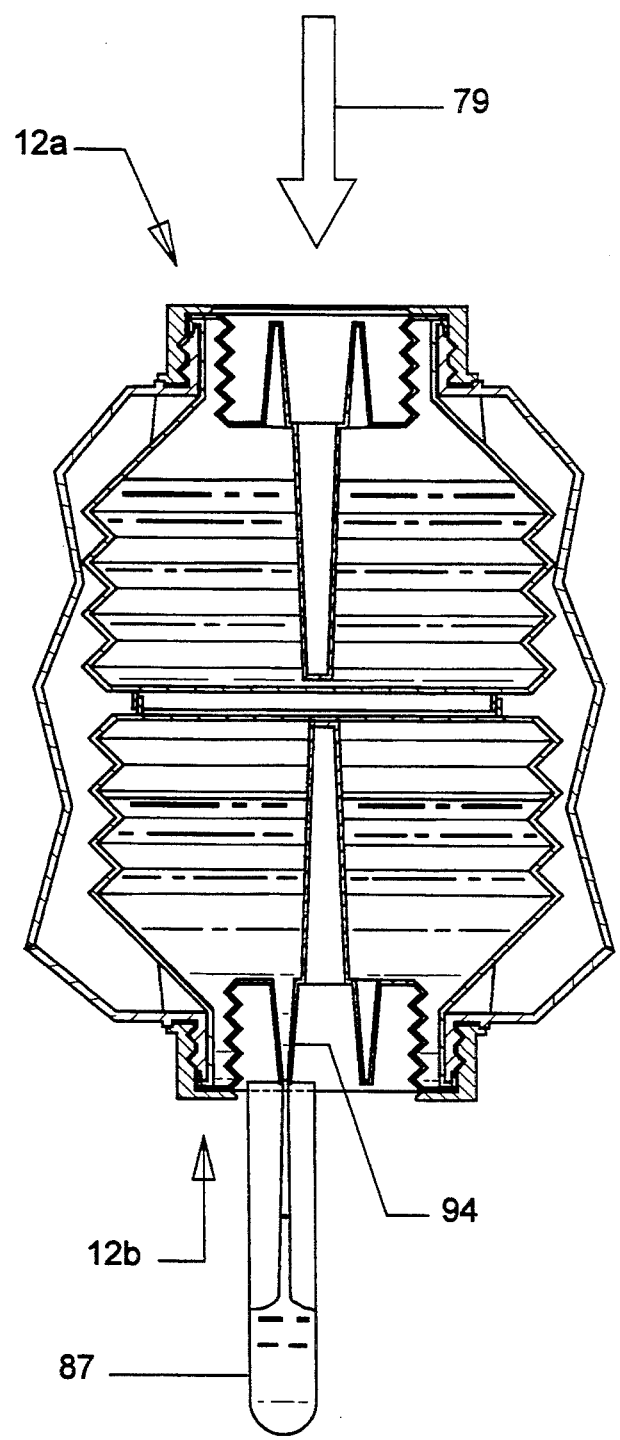
FIG. 17 is a schematic side vertical sectional view of the vessels of FIG. 16 with an arrow indicating a direction of force applied to the closure of the top container and showing filling of an aliquot tube with a liquid specimen from an accessed container.
Figure 18:
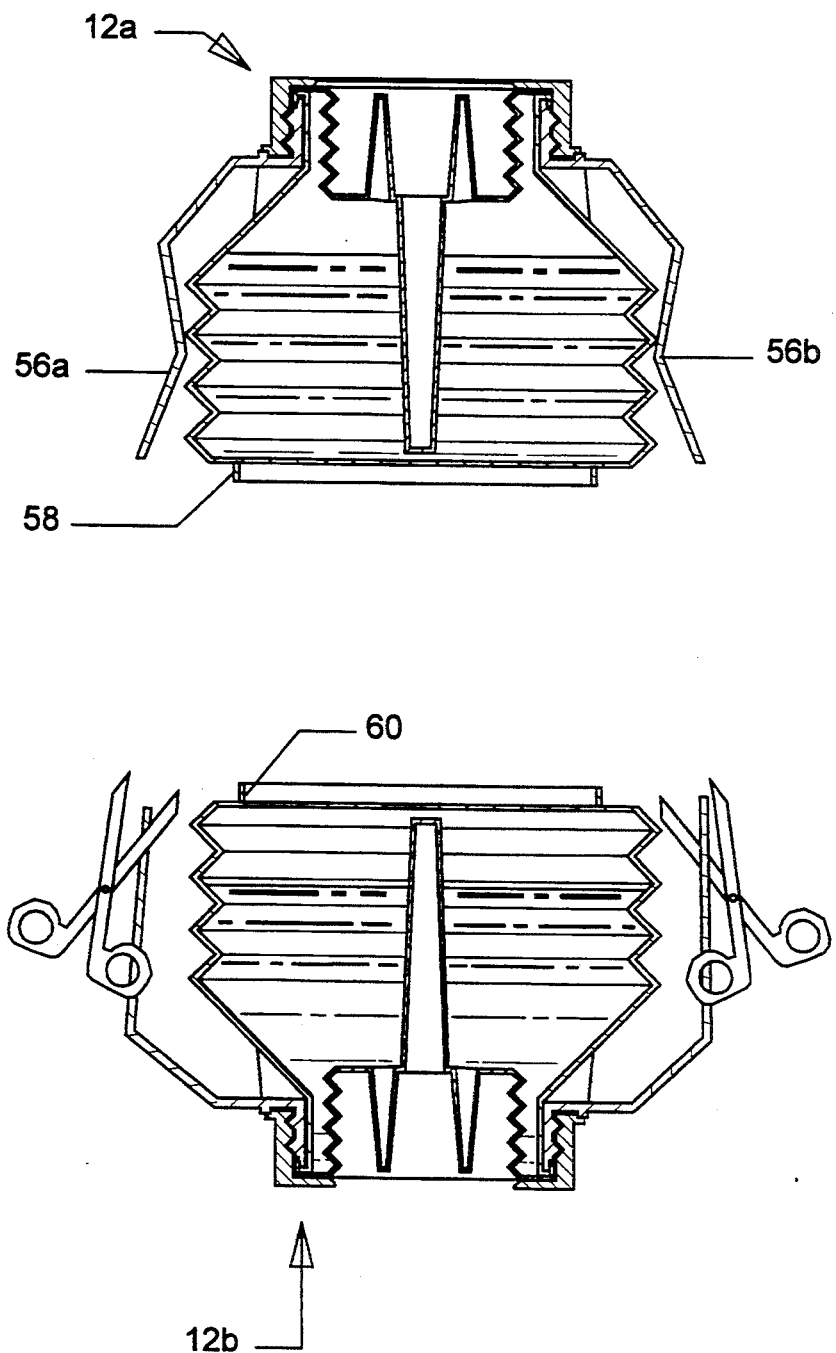
FIG. 18 is a schematic side vertical sectional view of the vessels of FIGS. 13–17 with scissors indicating severance of the serpentine portions of the retainer illustrated in FIG. 4 for separation of split liquid specimens.
Figures 19G, 19H:
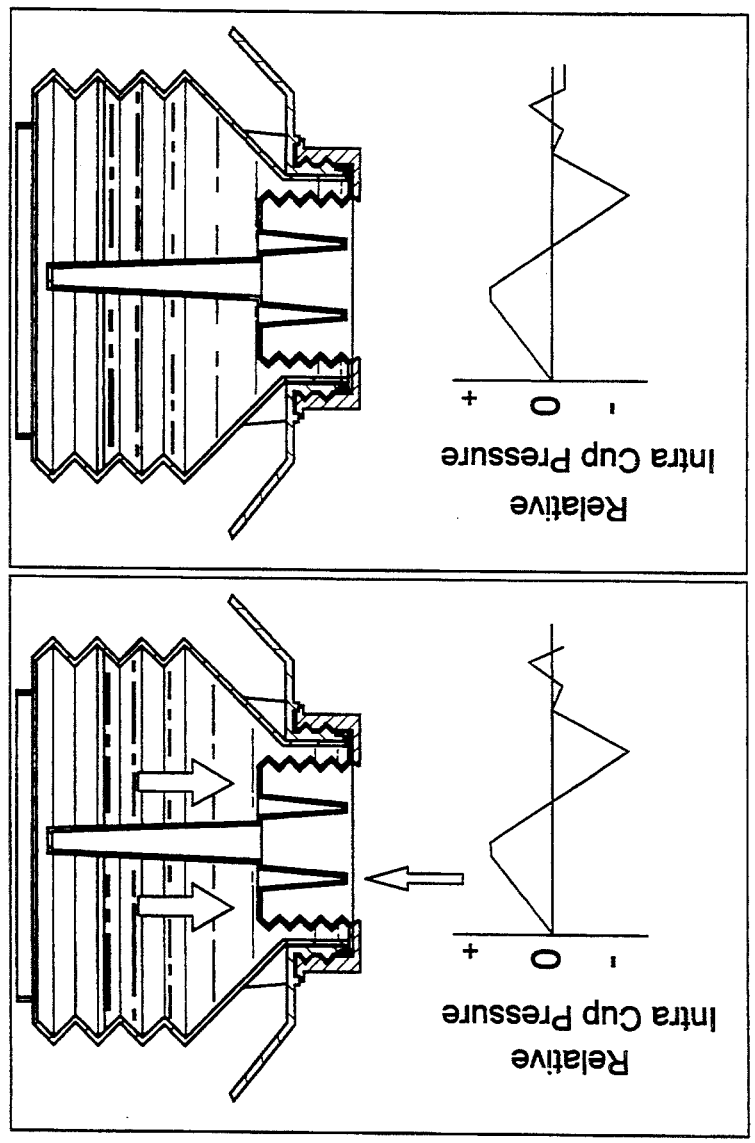

Next an aliquot tube 87 is placed under the opened nozzle 94, either by moving the aliquot tube 87 under the nozzle or by rotating the vessel assembly 10 to place the opened nozzle 94 over an aliquot tube. As depicted in FIG. 19f, base 82 of container 12b is then pushed upward (suitably by a mandrel inserted in projection 92), again shortening closure bellows 90 and increasing the pressure in container 12b, as shown by the line graph of FIG. 19f. This expels liquid from container 12b through nozzle 94 into aliquot tube 87, as also shown in FIG. 17. Then motion is reversed (FIG. 19g) and base 82 of container 12b is pulled down, increasing the intra-container volume of container 12b, shortening closure bellows 90 and decreasing the pressure in container 12b, as shown by the line graph of FIG. 19g. This draws air into nozzle 94, sweeping liquid from the nozzle.

Open nozzle 94 is then repositioned in line with the laser beam or air pencil axis. Exemplifying by use of a laser beam, the laser shutter is moved out of the laser beam path, and the laser is powered up. The laser lens is not placed in the path of the laser beam. With the shutter open, the laser emits a beam onto nozzle 94. This time the laser beam is unfocused and strikes the tip periphery of nozzle 94 as an unfocused column, melting the nozzle tip periphery. The lens shutter is then closed for a fraction of a second and reopened. The cessation of beam energy while the shutter is closed allows the nozzle tip melt to flow across the tip opening. The second burst of energy fuses the closure shut. After about another fraction of a second, the lens shutter is then closed again.

If the results of the sampling and testing by the first testing facility are questioned or challenged, containers 12a and 12b may be separated (while each maintains a sealed specimen within) by severing serpentine connectors 56a and 56b, and by gently rotating and/or rocking containers 12a and 12b relative to one another. The force this requires is more than a specimen vessel assembly would normally experience in normal handling but is slight enough to easily decoupling of the containers at members 58, 60. Then, container 12a with a liquid specimen contained therein is sent to another testing lab to confirm the results of the first tests. At the second testing lab, tamper evident tape 100 is removed from closure 80 of container 12a, and liquid specimen is withdrawn from container 12a by way of one of the nozzles 94.

Thus it will be apparent that this invention encompasses a method for liquid sampling which comprises (a) placing a specimen of a liquid into each of containers 12a and 12b fixed side by side by a retainer 34 including severable segments 46a and 46b interconnecting the two containers, each container 12 including stiff floor 14, sidewall 16 connected at a lower portion of the sidewall to the floor 14 and having an upper portion 20 including border 24 surrounding opening 28 into container 12, sidewall 16 further including flexure portion 32 below upper portion 20, thereof, and (b) closing first and second containers 12a and 12b with first and second closures 80a and 80b for containers 12a and 12b, each closure 80 including stiff base 82 smaller than opening 28 of the containers, with sidewall 84 connected at a lower portion of the sidewall to base 82, sidewall 84 including a flexure portion 90 below flange 88, base 82 having topside 83 and bottomside 85, bottomside 85 including a dependent stiff projection 92 of length to extend adjacent the container floor 14 upperside upon closure of container 12, the closure topside 83 including at least one upstanding nozzle opening 94 to closure bottomside 85, whereby said base bottomside projection 92 is positioned adjacent said container floor 14 upperside.

This method includes applicability where the segments 46a and 46b being severable and each container floor 14 having an upperside and an underside 57, the floor 14 of one vessel having on the underside 57 one member 58 of a coupling interlock pair and the floor 14 of the other container having on the underside 59 thereof the other member 60 of the coupling interlock pair, and in such instance further comprises (c) severing the severable segments 46a and 46b to release containers 12a and 12b from the fixed side-by-side position, and (d) coupling members 58 and 60 of the coupling interlock pair, so that the floor 14 of container 12a is connected to floor 14 of the container 12b.

The method includes applicability of funnel 60, and in step (a) includes placing the liquid specimen into entrance opening 66 of funnel 60 releasably connected to containers 12a and 12b, funnel 60 including wall 64 tapering inwardly from upper entrance opening 66 to two lower outlets 68 and. 70 positioned below funnel opening 66, funnel 60 between entrance opening 66 and outlets 68 and 70 having distributor 63 for distributing specimen to both said outlets 66 and 68. The method further comprises, after step (a) and before step (b), disconnecting said funnel from said vessel.

The method of the invention further includes withdrawal of an aliquot of liquid specimen from the closed vessel containing the liquid specimen. This method further comprises (e) pushing the closure base 12 of an inverted container, e.g. container 12b, filled as described above, while maintaining the container stationary, to extend flexure sidewalls 84 of the closure 80 and push the projection 92 of closure base 82 into contact with the inverted container floor 14 and to extend flexure sidewalls 32 of the inverted container, thereby to enlarge the volume of the inverted container, wherefore the intra-container pressure of the inverted container is reduced, (f) while maintaining the pressure imparted in step (e), creating an aperture in nozzle 94 of the inverted container to equilibrate the intrachamber pressure of the inverted container with ambient pressure, (g) pulling closure base 14 of the inverted container while maintaining the container stationary, to contract flexure sidewalls 84 of closure 80 and retract closure projection 92 of the inverted container from contact with the inverted container floor 14 and relax flexure sidewalls 32 of the inverted container, thereby to decrease the volume of the inverted container wherefore the intra-container pressure of the inverted container is increased insufficiently to expel liquid from the inverted container, and (h) pushing closure base 82 of the inverted container while maintaining the container stationary, to extend flexure sidewalls 84 of closure 80 insufficiently to cause the closure projection 92 of the inverted container to contact the inverted container floor 14, thereby to decrease the volume of the inverted container, wherefore the intra-container pressure of the inverted container is increased sufficiently to expel liquid from the inverted container.

Supplementing the foregoing method steps, the method further comprises (i) sealing the opened nozzle 94 of said inverted container, and in the case of the case where the containers 12a and 12b are coupled, also includes, after step (i), decoupling said members of said coupling pair to separate said containers. In the case where the retainer 34 comprises at least one serpentine connector 56a and/or 56b loosely connecting containers 12a and 12b, the method further comprises, after step (i), severing the serpentine connector.

As mentioned above, the term "adjacent" is intended to include not only an embodiment in which the end of projection 92 approaches near but does not contact the upperside of floor 14, as described in the method of operation just explained, but also the term includes an embodiment in which the end of projection 92 contacts the upperside of floor 14. A method of use of the latter embodiment differs from the first described method in that for the steps involving manipulation of the closed container, the operation is as follows.

Negative intra-container pressure relative to the ambient pressure is induced in container 12b by increasing the volume of container 12b. As depicted by arrow 77 in FIG. 16, this is accomplished by pushing closure base 82 toward floor 14 of container 12b. The vertically moveable or bellows portion 90 of closure 80 is extended by the push against base 82, allowing projection 92 in contact with floor 14 to move floor 14 away from base 82 by extending the vertically moveable or bellows sidewall portion 32. Any air entrapped in container 12b as at 104 is not materially compressed, because projection 92 already extends to floor 14 when base 82 is pushed. Thus movement of base 82 increases the volume of container 12b, and because container 12b is sealed, a negative intra-container pressure is induced relative to the ambient pressure. Movement of floor 14 of container 12b at the same time pushes coupled floor 14 of container 12b toward base 82 of container 12a. This push compresses vertically moveable or bellows portion 90 of closure 80 and vertically moveable or bellows sidewall portion 32 of container 12a and reduces the volume in container 12a. Any air entrapped in container 12a at 102 is compressed, and the volume of container 12a is decreased, increasing the intra-chamber pressure in container 12a. The stiffness of base 82 is sufficient to assure that nozzles 94 are maintained in a substantially vertical orientation for ease of opening.

With the negative pressure induced in container 12b maintained, a nozzle 94 is opened, preferably non-invasively as with the laser system or pencil column of heated air described above. After the nozzle is opened an aliquot tube 87 is placed under the opened nozzle 94, either by moving the aliquot tube 10 under the nozzle or by rotating the vessel assembly 10 to place the opened nozzle 94 over an aliquot tube. At the same time pressure is maintained or increased on closure base 82 of container 12b, assuring that no inadvertent distance closing movement occurs during location of the aliquot tube under the nozzle that could possibly reduce volume in container 12b sufficiently to expel some liquid from the container. Thus the bellows 32 and 90 of container 12b also provide the benefit of means for reduction of specimen cross contamination with other specimen specimens even with the nozzle tip open and pointing vertically downward.

Closure 80 of container 12a is then pushed downwardly toward container 12b, as indicated by the arrow 79 in FIG. 17. With bellows 32 and 90 of container 12a already compressed or preloaded, pushing closure 80 toward container 12b moves projection 92 of container 12a and thereby floor 14 of container 12a, thereby moving coupled floor 12b and compressing bellows 32 and 90 of container 12b. This reduces the volume of container 12b. The liquid specimen in the container is incompressible. The extent of movement of floor 14 is sufficient relative to the volume of liquid in the container to expel a volume of liquid from the container through the opened nozzle tip, as depicted in FIG. 17.

Thus in this embodiment, the method of this invention comprises after (a) placing a specimen of the stone liquid into each of first and second containers 12a and 12b as described for the first method and (b) closing the first and second containers 12a and 12b with first and second closures 80a and 80b for the containers as described above for the first method, the subsequent steps of (1) pressing on closure base 12 topside of container, e.g. 12b, of a filled vessel assembly 10 while maintaining the coupled container, e.g. 12a, in a fixed position, thereby pushing closure projection 92, floor 14 of container 12b, the coupled floor 14 of container 12a and the projection 92 of the closure 80 of container 12a, and thereby extending the moveable sidewall 84 of closure 80 of container 12b and the moveable sidewall 32 of container 12b and enlarging the volume of container 12b, and also thereby shortening the moveable sidewalls 32 and 84 of the container 12a and decreasing the volume of container 12a, whereby the intra-container pressure of container 12b is reduced and the intra-container pressure of container 12a is increased, (2) while maintaining the pressure imparted in step (e), creating an aperture in nozzle 94 of container 12b to equilibrate the intrachamber pressure of container 12b with ambient pressure, (3) pushing on the closure 80 of the second container while maintaining the coupled containers 12a and 12b in a fixed position, thereby pushing closure projection 92 of container 12a, the floor 14 of container 12a, the coupled floor 14 of container 12b and the projection 92 of closure 80 of container 12b and thereby lengthening the existing shortened moveable sidewall 90 of closure 80 of container 12a and the existing shortened moveable sidewall 32 of container 12a and increasing the existing reduced volume of container 12a, and also thereby shortening the existing extended moveable sidewall 90 of the closure 80 and the existing extended moveable sidewall 32 of container 12b and decreasing the existing enlarged volume of container 12b, whereby the intra-container pressure of the second container is increased above ambient pressure and an aliquot of liquid specimen in the first container is expelled from the first closure nozzle into an aliquot container, and (4) sealing the nozzle of said first container. The method of further comprises, after step (4), decoupling said members of said coupling pair to separate said containers, and where retainer 34 of vessel assembly 10 includes at least one serpentine connector loosely connecting the containers 12a and 12b, further comprises, after step (4), severing the serpentine connector.

The principles, preferred embodiment and mode of operation of the present invention have been described in the foregoing specification. The invention is not to be construed as limited to the particular forms disclosed, since these are regarded as illustrative rather than restrictive. Moreover, variations and changes may be made by those skilled in the art without deporting from the spirit of the invention.

I claim:
1. A liquid vessel, comprising:
   (a) a container including a stiff floor, a sidewall connected at a lower portion of the sidewall to the floor and having an upper portion including a rim surrounding an opening into the container, said sidewall further including a flexure portion below said upper portion thereof,
   (b) a closure for said container, said closure including a stiff base smaller than said opening and a sidewall connected at a lower portion of the sidewall to the base, said sidewall including a flexure portion, said base having a topside and a bottomside, said bottomside including a dependent stiff projection of length to extend adjacent said container floor upon closure of said container, said topside including at least one upstanding nozzle opening to said bottomside.

2. An assembly of the liquid vessel of claim 1 comprising a first said container and closure, a second said container and closure, and a retainer interconnecting said first and second containers, at least a portion of the retainer fixing the containers side-by-side.

3. The liquid vessel assembly of claim 2, each said container floor having an upperside and an underside, the floor of one container having on the underside thereof one member of a coupling interlock pair and the floor of the other container having on the underside thereof the other member of a coupling interlock pair.

4. The liquid vessel assembly of claim 2 wherein said fixing portion of said retainer is severable.

5. The liquid vessel assembly of claim 4 wherein in addition to said fixing portion said retainer comprises at least one connector loosely connecting the first and second containers.

6. The liquid vessel assembly of claim 2 further comprising a funnel for connection thereto, said funnel including a wall tapering inwardly from an upper entrance opening to two lower outlets positioned below said funnel opening, said funnel between said entrance opening and said outlets having a distributor for distributing to both said outlets a liquid admitted through the funnel entrance opening, said fixing portion of said retainer including one member of at least one pair of companion means for releasably connecting said funnel to said fixing portion in position to empty liquid from said funnel outlets into said container openings in the absence of said container closures, said funnel exteriorly of said funnel wall having the other member of said companion means for releasable connection of said funnel to said fixing portion of said retainer.

7. The liquid vessel assembly of claim 6, wherein the funnel includes a handle extending in substantially the direction of a line connecting the axes of the funnel outlets.

8. The liquid vessel assembly of claim 1 further comprising means on said closure operative with means on said container for sealingly securing said closure to said container.

9. The liquid vessel assembly of claim 8, wherein said sidewall includes an upper portion comprising a flange radially extending thereby to rest on said rim of said container.

10. The liquid vessel assembly of claim 9 in which at least the upper portion of said sidewall of said container comprises a deformable material, said rim of said container comprises a gasket, said fixing portion of said retainer includes an upright portion surrounding an upper portion of the container between said rim and said flexure portion of said sidewall, said upright portion supports said rim and has threads formed exteriorly thereon, and said closure includes a depending flange having threads formed thereon cooperative with the threads on said retainer.

11. The liquid vessel assembly of claim 9 in which at least the upper portion of said sidewall of said container comprises a rigid material having threads formed exteriorly thereon and said closure includes a down flange having threads formed thereon cooperative with the threads on said container.

12. The liquid vessel assembly of claim 8 in which the fixing portion of said retainer includes a ratchet reverse turn stop and said closure includes a ratchet member slideable over said stop in the forward turn direction only, said forward turn direction being the direction in which said closure is turned to screw said closure by said threads onto said container.

13. A split specimen liquid vessel assembly, comprising:
(a) first and second containers, each container including a stiff floor, a sidewall connected at a lower portion of the sidewall to the floor and having an upper portion including a rim surrounding an opening into the container, said sidewall further including a flexure portion below said upper portion thereof, each said container floor having an upperside and an underside, the floor of one vessel having on the underside thereof one member of a coupling interlock pair and the floor of the other container having on the underside thereof the other member of a coupling interlock pair,
(b) first and second closures for said containers, each said closure including a stiff base smaller than said opening of said containers, a sidewall connected at a lower portion of the sidewall to the base, said sidewall having an upper portion comprising a flange radially extending further than said base to rest on said rim of a said container, said sidewall further including a flexure portion below said flange, said base having a topside and a bottomside said bottomside including a dependent stiff projection of length to extend to said container floor upon closure of said container, said topside including at least one upstanding nozzle opening to said bottomside,
(c) means on said closure operative with means on said container for sealingly securing said closure to said container, and
(d) a retainer connecting said first and second containers, at least a portion of the retainer fixing the containers horizontally side-by-side, said retainer further comprising at least one serpentine connector loosely connecting the first and second containers.

14. The split specimen liquid vessel assembly of claim 13, further comprising:
(e) a funnel for connection to said vessel, said funnel including a wall tapering inwardly from an upper entrance opening to two lower outlets positioned below said funnel opening, said funnel between said entrance opening and said outlets having a distributor for distributing to both said outlets a liquid admitted through the funnel entrance opening, said fixing portion of said retainer including one member of at least one pair of companion means for releasably connecting said funnel to said fixing portion in position to empty liquid from said funnel outlets into said container openings in the absence of said container closures, said funnel having the other member of at said least one companion means exteriorly of said funnel wall for releasable connection of said funnel to said retainer.

15. A method of collecting a liquid sample, comprising:
(a) placing a specimen of a liquid into each of first and second containers fixed side by side by a retainer including a severable segment interconnecting the two containers, each container including a stiff floor, a sidewall connected at a lower portion of the sidewall to the floor and having an upper portion including a rim surrounding an opening into the container, said sidewall further including a flexure portion below said upper portion thereof,
(b) closing the first and second containers with first and second closures for said containers, each said closure including a stiff base smaller than said opening of said containers, a sidewall connected at a lower portion of the sidewall to the base, said sidewall including a flexure portion below said flange, said base having a topside and a bottomside, said bottomside including a dependent stiff projection of length to extend adjacent said container floor upperside upon closure of said container, said closure topside including at least one upstanding nozzle opening to said closure bottomside, whereby said base bottomside projection is positioned adjacent said container floor upperside.

16. The method of claim 15 in which said step (a) includes placing said specimen into an entrance opening of a funnel releasably connected to said vessel, said funnel including a wall tapering inwardly from said upper entrance opening to two lower outlets positioned below said funnel opening, said funnel between said entrance opening and said outlets having a distributor for distributing said specimen to both said outlets, and further comprising, after step (a) and before step (b), disconnecting said funnel from said vessel.

17. The method of claim 15 in which said segment is severable and each said container floor has an upperside and an underside, the floor of one vessel having on the underside thereof one member of a coupling interlock pair and the floor of the other container having on the underside thereof the other member of a coupling interlock pair, further comprising:
(c) severing said severable segment to release the first and second containers from said fixed side-by-side position, and
(d) coupling said members of said coupling interlock pair, so that the floor of the first container is connected to the floor of the second container.

18. The method of claim 17, in which further comprises:
(e) pushing the closure base of an inverted one of said first and second containers filled in accordance with the method of claim 15 while maintaining the inverted container stationary, to extend said flexure sidewalls of the closure and push said projection of said closure base of said inverted container into contact with the inverted container floor and to extend said flexure sidewalls of the inverted container, thereby to enlarge the volume of the inverted container, wherefore the intra-container pressure of the inverted container is reduced,
(f) while maintaining the pressure imparted in step (e), creating an aperture in said nozzle of the said container to equilibrate the intrachamber pressure of the inverted container with ambient pressure,
(g) pulling said closure base of said inverted container while maintaining the container stationary, to contract said flexure sidewalls of the closure and retract said closure projection of said inverted container from contact with the inverted container floor and relax said flexure sidewalls of the inverted container, thereby to decrease the volume of the inverted container wherefore the intra-container pressure of the inverted container is increased insufficiently to expel liquid from said inverted container, and
(h) pushing said closure base of said inverted container while maintaining the container stationary, to extend said flexure sidewalls of the closure insufficiently to cause said closure projection of said inverted container to contact with the inverted container floor, thereby to decrease the volume of the inverted container, wherefore the intra-container pressure of the inverted container is increased sufficiently to expel liquid from said inverted container.

19. The method of claim 18 further comprising (i) sealing the opened nozzle of said inverted container.

20. The method of claim 19 comprising, after step (i), decoupling said members of said coupling pair to separate said containers.

21. The method of claim 20 in which said retainer of said vessel further comprises at least one serpentine connector loosely connecting the first and second containers, and wherein said method further comprises after step (i), severing said serpentine connector.

22. The method of claim 17, which further comprises:
(e) pressing on the closure base topside of a first container of a vessel filled in accordance with the method of claim 15 while maintaining the coupled first and second containers of said vessel in a fixed position, thereby pushing said first closure projection, the floor of the first container, the coupled floor of the second container and the projection of the second closure and thereby extending the moveable sidewall of the first closure and the moveable sidewall of the first container and enlarging the volume of the first container, and also thereby shortening the moveable sidewall of the second closure and the moveable sidewall of the second container and decreasing the volume of the second container, wherefore the intra-container pressure of the first container is reduced and the intracontainer pressure of the second container is increased,
(f) while maintaining the pressure imparted in step (e), creating an aperture in said nozzle of the said container to equilibrate the intrachamber pressure of the first container with ambient pressure,
(g) pushing on the closure base topside of the second container while maintaining the coupled first and second containers in a fixed position, thereby pushing said second closure projection, the floor of the second container, the coupled floor of the first container and the projection of the first closure and thereby lengthening the existing shortened moveable sidewall of the second closure and the existing shortened moveable sidewall of the second container and increasing the existing reduced volume of the second container, and also thereby shortening the existing extended moveable sidewall of the first closure and the existing extended moveable sidewall of the first container and decreasing the existing enlarged volume of the first container, wherefore the intra-container pressure of the second container is increased above ambient pressure and an aliquot of liquid specimen in the first container is expelled from the first closure nozzle into an aliquot container, and
(h) sealing the nozzle of said first container.

23. The method of claim 22 comprising, after step (k), decoupling said members of said coupling pair to separate said containers.

24. The method of claim 23 in which said retainer of said vessel further comprises at least one serpentine connector loosely connecting the first and second containers, and wherein said method further comprises after step (k), severing said serpentine connector.

* * * * *